(12) United States Patent
Gualberto et al.

(10) Patent No.: US 10,980,793 B2
(45) Date of Patent: *Apr. 20, 2021

(54) METHODS OF TREATING CANCER WITH FARNESYLTRANSFERASE INHIBITORS

(71) Applicant: Kura Oncology, Inc., San Diego, CA (US)

(72) Inventors: Antonio Gualberto, Acton, MA (US); Catherine Rose Scholz, North Reading, MA (US)

(73) Assignee: KURA ONCOLOGY, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/541,063

(22) Filed: Aug. 14, 2019

(65) Prior Publication Data

US 2020/0000796 A1 Jan. 2, 2020

Related U.S. Application Data

(63) Continuation of application No. 15/946,578, filed on Apr. 5, 2018, now Pat. No. 10,426,767, which is a continuation of application No. 15/820,157, filed on Nov. 21, 2017, now Pat. No. 9,956,215.

(60) Provisional application No. 62/519,819, filed on Jun. 14, 2017, provisional application No. 62/507,749, filed on May 17, 2017, provisional application No. 62/461,602, filed on Feb. 21, 2017.

(51) Int. Cl.
*A61K 31/4709* (2006.01)
*A61K 45/06* (2006.01)

(52) U.S. Cl.
CPC .......... *A61K 31/4709* (2013.01); *A61K 45/06* (2013.01)

(58) Field of Classification Search
CPC .............................. A61K 31/4709; A61K 45/06
USPC ....................................................... 514/312
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,016,043 A | 4/1977 | Schuurs et al. |
| 4,018,653 A | 4/1977 | Mennen |
| 4,044,126 A | 8/1977 | Cook et al. |
| 4,328,245 A | 5/1982 | Yu et al. |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,424,279 A | 1/1984 | Bohn et al. |
| 4,870,287 A | 9/1989 | Cole et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,210,015 A | 5/1993 | Gelfand et al. |
| 5,310,652 A | 5/1994 | Gelfand et al. |
| 5,322,770 A | 6/1994 | Gelfand et al. |
| 5,323,907 A | 6/1994 | Kalvelage |
| 5,354,556 A | 10/1994 | Sparks et al. |
| 5,399,491 A | 3/1995 | Kacian et al. |
| 5,409,818 A | 4/1995 | Davey et al. |
| 5,437,990 A | 8/1995 | Burg et al. |
| 5,455,166 A | 10/1995 | Walker |
| 5,487,972 A | 1/1996 | Gelfand et al. |
| 5,491,063 A | 2/1996 | Fisher et al. |
| 5,561,058 A | 10/1996 | Gelfand et al. |
| 5,571,673 A | 11/1996 | Picone et al. |
| 5,591,767 A | 1/1997 | Mohr et al. |
| 5,639,476 A | 6/1997 | Oshlack et al. |
| 5,639,480 A | 6/1997 | Bodmer et al. |
| 5,641,864 A | 6/1997 | Gelfand |
| 5,674,533 A | 10/1997 | Santus et al. |
| 5,693,517 A | 12/1997 | Gelfand et al. |
| 5,733,566 A | 3/1998 | Lewis |
| 5,739,108 A | 4/1998 | Mitchell |
| 5,760,395 A | 6/1998 | Johnstone |
| 5,804,375 A | 9/1998 | Gelfand et al. |
| 5,874,442 A | 2/1999 | Doll et al. |
| 5,891,474 A | 4/1999 | Busetti et al. |
| 5,922,356 A | 7/1999 | Koseki et al. |
| 5,972,891 A | 10/1999 | Kamei et al. |
| 5,980,945 A | 11/1999 | Ruiz |
| 5,993,855 A | 11/1999 | Yoshimoto et al. |
| 6,045,830 A | 4/2000 | Igari et al. |
| 6,087,324 A | 7/2000 | Igari et al. |
| 6,113,943 A | 9/2000 | Okada et al. |
| 6,197,350 B1 | 3/2001 | Yamagata et al. |
| 6,248,363 B1 | 6/2001 | Patel et al. |
| 6,264,970 B1 | 7/2001 | Hata et al. |
| 6,267,981 B1 | 7/2001 | Okamoto et al. |

(Continued)

FOREIGN PATENT DOCUMENTS

| | | |
|---|---|---|
| WO | WO 1992/008800 | 5/1992 |
| WO | WO 1993/018186 | 9/1993 |
| WO | WO 1994/010138 | 5/1994 |
| WO | WO 1997/030992 | 8/1997 |
| WO | WO 1998/028303 | 7/1998 |

(Continued)

OTHER PUBLICATIONS

Abramson et al, "Nucleic acid amplification technologies," Current Opinion in Biotechnology 4:41-47 (1993).

(Continued)

*Primary Examiner* — Yevgeny Valenrod
(74) *Attorney, Agent, or Firm* — Jones Day

(57) ABSTRACT

The present invention relates to the field of cancer therapy. Specifically, provided are methods of treating cancer, for example, peripheral T-cell lymphoma ("PTCL"), with a farnesyltransferase inhibitor (FTI) that include determining whether the subject is likely to be responsive to the FTI treatment based on gene expression characteristics.

30 Claims, 10 Drawing Sheets

(56) References Cited

U.S. PATENT DOCUMENTS

| | | | |
|---|---|---|---|
| 6,376,461 | B1 | 4/2002 | Igari et al. |
| 6,419,961 | B1 | 7/2002 | Igari et al. |
| 6,545,020 | B1 | 4/2003 | Van Ginckel et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 6,838,467 | B2 | 1/2005 | End |
| 6,927,024 | B2 | 8/2005 | Dodge et al. |
| 7,101,663 | B2 | 9/2006 | Godfrey et al. |
| 7,122,799 | B2 | 10/2006 | Hsieh et al. |
| 7,186,507 | B2 | 3/2007 | Bacallao et al. |
| 8,603,477 | B2 | 12/2013 | Afar et al. |
| 9,956,215 | B1 * | 5/2018 | Gualberto .............. A61K 45/06 |
| 10,137,121 | B2 | 11/2018 | Gualberto et al. |
| 10,426,767 | B2 * | 10/2019 | Gualberto .............. A61K 45/06 |
| 2007/0093449 | A1 | 4/2007 | De Porre et al. |

FOREIGN PATENT DOCUMENTS

| | | |
|---|---|---|
| WO | WO 1999/045712 | 9/1999 |
| WO | WO 2000/001691 | 1/2000 |
| WO | WO 2000/012498 | 3/2000 |
| WO | WO 2000/012499 | 3/2000 |
| WO | WO 2017/184968 | 10/2017 |
| WO | WO 2018/156609 | 8/2018 |

OTHER PUBLICATIONS

Angerer et al., "In Situ Hybridization to Cellular RNAs," Genetic Engineering: Principles and Methods, 7:43-65 (1985).
Buchwald et al., "Long-term, continuous intravenous heparin administration by an implantable infusion pump in ambulatory patients with recurrent venous thrombosis," Surgery 88:507 (1980).
Bustin, et al., "Real-time reverse transcription PCR (qRT-PCR) and its potential use in clinical diagnosis," 2005, Clin. Sci., 109:365-379.
Carstensen, Drug Stability: Principles & Practice, 2d. Ed., Marcel Dekker, NY, NY, 1995, pp. 379-380.
Chen et al., "Salt-inducible kinase 3 is a novel mitotic regulator and a target for enhancing antimitotic therapeutic mediated cell death," 2014, Cell Death and Disease 5:e1177.
Cheng et al., "Memorial Sloan Kettering-Integrated Mutation Profiling of Actionable Cancer Targets (MSK-IMPACT)," J Mol Diagn. ,17(3):251-264(2015).
Elhamri et al., "Tipifarnib in the treatment of acute myeloid leukemia," Biologics, 1(4):415-424 (2007).
Gall et al., "Nucleic Acid Hybridization in Cytological Preparations," Meth. Enzymol., 21:470-480 (1981).
Goodson, "The Scope of Dental Therapy," Medical Applications of Controlled Release, vol. 2, pp. 115-138 (1984).
Guatelli et al., "Isothermal, in vitro amplification of nucleic acids by a multienzyme reaction modeled after retroviral replication," Proc. Natl. Acad. Sci. USA 87: 1874-1878, 1990.
Hod, "A Simplified Ribonuclease Protection Assay," Biotechniques 13:852-854 (1992).
Holland et al., "Detection of specific polymerase chain reaction product by utilizing the 5' to 3' exonuclease activity of Thermus aquaticus DNA polymerase," 1988, Proc. Natl. Acad. Sci. USA 88:7276-7280.
Hussein et al., "Farnesylation of Cenp-F is required for G2/M progression and degradation after mitosis," 2002, J. Cell Sci. 115:3403-3414.
Iqbal et al., "Gene expression signatures delineate biological and prognostic subgroups in peripheral T-cell lymphoma," Blood 123(19): 2915-23 (2014).
Kallioniemi et al., "Comparative Genomic Hybridization for Molecular Cytogenetic Analysis of Solid Tumors," Science 258:818-821 (1992).
Kamarck, "Fluorescence-Activated Cell Sorting of Hybrid and Transfected Cells," 1987, Methods Enzymol, 151:150-165.
Kent, W., "BLAT—The Blast-Like Alignment Tool," Genome Res. 12(4):656-64 (2002).
Kirschbaum et al., "APhase 1 Trial Dose Escalation Study of Tipifarnib on a Week-On, Week-Off Schedule in Relapsed, Refractory or High-Risk Myeloid Leukemia," Leukemia, 25(10):1543-1547 (2011).
Kramer et al., "Replicatable RNA reporters," Nature 339:401-402, 1989.
Kwoh et al., "Transcription-based amplification system and detection of amplified human immunodeficiency virus type 1 with a bead-based sandwich hybridization format," Proc. Natl. Acad. Sci. USA 86: 1173-1177, 1989.
Langer, "New Methods of Drug Delivery," Science 249:1527-1533 (1990).
Lara et al., "Intermittent dosing of the farnesyl transferase inhibitor tipifarnib (R115777) in advanced malignant solid tumors: a phase I California Cancer Consortium Trial," Anticancer Drugs, 16(3):317-321 (2005).
Lomeli et al., "Quantitative Assays Based on the Use of Replicatable Hybridization Probes," Clin. Chem. 35: 1826-1831, 1989.
Maher et al., "Transcriptome sequencing to detect gene fusions in cancer," Nature 458 (7234): 97-101 (Jan. 2009).
Parker et al., "mRNA: Detection by In Situ and Northern Hybridization," Methods in Molecular Biology 106:247-283 (1999).
Pitt et al., "CXCL12-Producing Vascular Endothelial Niches Control Acute T Cell Leukemia Maintenance," 2015, Cancer Cell 27:755-768.
Rozen et al., "Primer3 on the WWW for General Users and for Biologist Programmers," Bioinformatics Methods and Protocols: Methods in Molecular Biology . Humana Press, Totowa, N.J., pp. 365-386 (1999).
Ryan et al., "Profiling the HeLa S3 transcriptome using randomly primed cDNA and massiveley parallel short-read sequencing," BioTechniques 45 (1): 81-94 (2008).
Saudek et al., "A Preliminary Trial of the Programmable Implantable Medication System for Insulin Delivery," N. Engl. J. Med. 321:574 (1989).
Schena et al., "Parallel human genome analysis: Microarray-based expression monitoring of 1000 genes," Proc. Natl. Acad. Sci. USA 93(2): 106-149 (1996).
Sefton, "Implantable Pumps," CRC Crit. Ref. Biomed. Eng. 14:201 (1987).
Thomas et al., "Tipifarnib in the treatment of acute myeloid leukemia," *Biologics*, 1(4):415-424 (2007).
United States Patent and Trademark Office, Notice of Allowance issued in U.S. Appl. No. 15/820,012, dated Oct. 17, 2018.
United States Patent and Trademark Office, Notice of Allowance issued in U.S. Appl. No. 15/820,157, dated Mar. 20, 2018.
United States Patent and Trademark Office, Office Action issued in U.S. Appl. No. 15/820,012, dated May 7, 2018.
Velculescu et al., "Characterization of the Yeast Transcriptome," Cell 88:243-51 (1997).
Velculescu et al., "Serial Analysis of Gene Expression," Science 270:484-487 (1995).
Walker et al., "Isothermal in vitro amplification of DNA by a restriction enzyme/DNA polymerase system," Proc. Natl. Acad. Sci. USA 89:392-396, 1992.
Walkinshaw et al., "The Tumor Suppressor Kinase LKB1 Activates the Downstream Kinases SIK2 and SIK3 to Stimulate Nuclear Export of Class IIa Histone Deacetylases," 2013, J. Biol. Chem. 288:9345-9362.
Wang et al., "RNA-Seq: a revolutionary tool for transcriptomics," Nature Reviews Genetics, 10 (1): 57-63 (Jan. 2009).
Weis et al., "Detection of rare mRNAs via quantitative RT-PCR," Trends in Genetics, 8:263-264 (1992).
Witzig et al, "The CXCL1 2/CXCR4 Pathway As a Potential Target of Tipifarnib: Preliminary Results from an Open-Label, Phase II Study in Relapsed or Refractory Peripheral T-Cell Lymphoma," Blood, 130(Supp. 1):2788 (2017).

(56) References Cited

OTHER PUBLICATIONS

Witzig et al., "Multi-institutional phase 2 study of the farnesyltransferase inhibitor tipifarnib (R115777) in patients with relapsed and refractory lymphomas," Blood, 118(18):4882-4889 (2011).
Wu et al., "The Ligation Amplification Reaction (LAR)—Amplification of Specific DNA Sequences Using Sequential Rounds of Template-Dependent Ligation," Genomics, 4:560-569, 1988.
Zhang et al., "Therapeutic options in peripheral T cell lymphoma," J. Hematol. Oncol., 9:37 (2016).
Zhao et al., "Epstein-Barr virus nuclear antigen 3C regulated genes in lymphoblastoid cell lines," 2011, Proc. Natl. Acad. Sci. USA, 108:337-342.
Zujewski et al., "Phase I and Pharmacokinetic Study of Farnesyl Protein Transferase Inhibitor R115777 in Advanced Cancer," J Clin Oncol., 18(4):927-941 (2000).
International Search Report and Written Opinion issued in International Patent Application No. PCT/US2018/018989, dated May 30, 2018.
Karp et al., "Clinical and biologic activity of the farnesyltransferase inhibitor R115777 in adults with refractory and relapsed acute leukemias: a phase 1 clinical-laboratory correlative trial," *Blood*, 97(11):3361-3369 (2001).
United States Patent and Trademark Office, Notice of Allowance issued in U.S. Appl. No. 15/820,157, dated Feb. 5, 2018.
United States Patent and Trademark Office, Office Action issued in U.S. Appl. No. 15/946,578, dated May 28, 2019.
United States Patent and Trademark Office, Notice of Allowance issued in U.S. Appl. No. 15/946,578, dated Jul. 23, 2019.

\* cited by examiner

METHODS OF TREATING CANCER WITH FARNESYLTRANSFERASE INHIBITORS

RELATED APPLICATIONS

This application is a continuation of U.S. application Ser. No. 15/946,578, filed Apr. 5, 2018, which is a continuation of U.S. application Ser. No. 15/820,157, filed Nov. 21, 2017, now U.S. Pat. No. 9,956,215, which claims the benefit of U.S. Ser. Nos. 62/519,819 filed Jun. 14, 2017, 62/507,749 filed May 17, 2017, and 62/461,602 filed Feb. 21, 2017, the disclosures of each of which are incorporated by reference herein in their entirety.

FIELD

The present invention relates to the field of cancer therapy. In particular, provided are methods of treating cancer with farnesyltransferase inhibitors.

BACKGROUND

Stratification of patient populations to improve therapeutic response rate is increasingly valuable in the clinical management of cancer patients. Farnesyltransferase inhibitors (FTI) are therapeutic agents that have utility in the treatment of cancers, such asperipheral T-cell lymphoma ("PTCL"). However, patients respond differently to an FTI treatment. Therefore, methods to predict the responsiveness of a subject having cancer to an FTI treatment, or methods to select cancer patients for an FTI treatment, represent unmet needs. The methods and compositions provided herein meet these needs and provide other related advantages.

SUMMARY

Provided herein are methods to treat CXCL12-expressing cancer in a subject including administering a therapeutically effective amount of an FTI to the subject having a CXCL12-expressing cancer. Provided herein are also methods to predict the responsiveness of a subject having cancer for an FTI treatment, methods to select a cancer patient for an FTI treatment, methods to stratify cancer patients for an FTI treatment, and methods to increase the responsiveness of a cancer patient population for an FTI treatment. In some embodiments, the methods include analyzing a sample from the subject having cancer to determining that the subject has CXCL12-expressing cancer prior to administering the FTI to the subject. In some embodiments, the FTI is tipifarnib. In specific embodiments, the cancer is nasopharyngeal carcinoma. In specific embodiments, the cancer is EBV associated nasopharyngeal carcinoma. In specific embodiments, the cancer is esophageal cancer. In specific embodiments, the cancer is ovarian cancer. In specific embodiments, the cancer is a sarcoma. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is cutaneous T-Cell lymphoma (CTCL). In certain embodiments, the cancer is leukemia. In specific embodiments, the leukemia is acute myeloid leukemia (AML). In specific embodiments, the leukemia is T-cell acute lymphoblastic leukemia (T-ALL). In specific embodiments, the leukemia is chronic myelogenous leukemia (CML).

Provided herein are methods to treat CXCL12-expressing lymphoma in a subject including administering a therapeutically effective amount of an FTI to the subject having a CXCL12-expressing lymphoma. Provided herein are also methods to predict the responsiveness of a subject having lymphoma for an FTI treatment, methods to select a lymphoma patient for an FTI treatment, methods to stratify lymphoma patients for an FTI treatment, and methods to increase the responsiveness of a lymphoma patient population for an FTI treatment. In some embodiments, the methods include analyzing a sample from the subject having lymphoma to determine that the subject has CXCL12-expressing lymphoma prior to administering the FTI to the subject. In some embodiments, the FTI is tipifarnib. In specific embodiments, the lymphoma is an EBV associated lymphoma. In specific embodiments, the lymphoma is angioimmunoblastic T-cell lymphoma (AITL). In specific embodiments, the lymphoma is CTCL.

Provided herein are methods to treat CXCL12-expressing leukemia in a subject including administering a therapeutically effective amount of an FTI to the subject having a CXCL12-expressing leukemia. Provided herein are also methods to predict the responsiveness of a subject having leukemia for an FTI treatment, methods to select a leukemia patient for an FTI treatment, methods to stratify leukemia patients for an FTI treatment, and methods to increase the responsiveness of a leukemia patient population for an FTI treatment. In some embodiments, the methods include analyzing a sample from the subject having leukemia to determine that the subject has CXCL12-expressing leukemia prior to administering the FTI to the subject. In some embodiments, the FTI is tipifarnib. In specific embodiments, the leukemia is T-ALL. In specific embodiments, the leukemia is CML.

Provided herein are methods to treat CXCL12-expressing acute myeloid leukemia (AML) in a subject including administering a therapeutically effective amount of an FTI to the subject having a CXCL12-expressing AML. Provided herein are also methods to predict the responsiveness of a subject having AML for an FTI treatment, methods to select an AML patient for an FTI treatment, methods to stratify AML patients for an FTI treatment, and methods to increase the responsiveness of an AML patient population for an FTI treatment. In some embodiments, the methods include analyzing a sample from the subject having AML to determining that the subject has CXCL12-expressing AML prior to administering the FTI to the subject. In some embodiments, the FTI is tipifarnib. In specific embodiments, the AML is newly diagnosed AML. In specific embodiments, the subject having AML is an elderly patient with poor-risk AML. In specific embodiments, the AML is relapsed or refractory AML.

Provided herein are methods to treat AITL in a subject including administering a therapeutically effective amount of an FTI to the subject having AITL. Provided herein are also methods to predict the responsiveness of a subject having AITL for an FTI treatment, methods to select an AITL patient for an FTI treatment, methods to stratify AITL patients for an FTI treatment, and methods to increase the responsiveness of an AITL patient population for an FTI treatment. In some embodiments, the methods include analyzing a sample from the subject having AITL to determine that the subject has AITL histology prior to administering the FTI to the subject. In some embodiments, the FTI is tipifarnib. In some embodiments, the AITL histology is characterized by a tumor cell component. In certain embodiments, the tumor cell component comprises polymorphous medium-sized neoplastic cells derived from follicular helper T cells. In some embodiments, the AITL histology is characterized by a non-tumor cell component. In certain embodiments, the non-tumor cell component comprises prominent arborizing blood vessels. In certain embodiments, the non-tumor cell component comprises proliferation of follicular dendritic cells. In certain embodiments, the non-tumor cell component comprises scattered EBV positive B-cell blasts. In certain embodiments, the subject has been diagnosed with AITL. In certain embodiments, diagnosis with AITL comprises visualization of a non-tumor component. In certain embodiments, diagnosis with AITL comprises visualization of proliferation of endothelial venules. In certain embodiments, diagnosis with AITL comprises detecting the presence of one or more of the following tumor markers: CXCL13, CD10, PD1, and BCL6. In some embodiments, the methods provided herein include characterizing the histology in a sample from a subject having lymphoma, and administering a therapeutically effective amount of an FTI to the subject if the subject has an AITL histology.

Provided herein are methods to treat CXCL12-expressing PTCL in a subject including administering a therapeutically effective amount of an FTI to the subject having a CXCL12-expressing PTCL. Provided herein are also methods to predict the responsiveness of a subject having PTCL for an FTI treatment, methods to select a PTCL patient for an FTI treatment, methods to stratify PTCL patients for an FTI treatment, and methods to increase the responsiveness of a PTCL patient population for an FTI treatment. In some embodiments, the methods include analyzing a sample from the subject having PTCL to determining that the subject has CXCL12-expressing PTCL prior to administering the FTI to the subject. In some embodiments, the FTI is tipifarnib. In some embodiments, the PTCL is angioimmunoblastic T-cell lymphoma (AITL), PTCL not otherwise specified (PTCL-NOS), anaplastic large cell lymphoma (ALCL)-anaplastic lymphoma kinase (ALK) positive, ALCL-ALK negative, enteropathy-associated T-cell lymphoma, extranodal natural killer cell (NK) T-cell lymphoma-nasal type, hepatosplenic T-cell lymphoma, or subcutaneous panniculitis-like T-cell lymphoma. In specific embodiments, the PTCL is AITL or PTCL-NOS. In specific embodiments, the PTCL is AITL.

Provided herein are methods to treat CXCL12-expressing myelodysplastic syndrome (MDS) in a subject including administering a therapeutically effective amount of an FTI to the subject having CXCL12-expressing MDS. Provided herein are also methods to predict the responsiveness of a subject having MDS for an FTI treatment, methods to select an MDS patient for an FTI treatment, methods to stratify MDS patients for an FTI treatment, and methods to increase the responsiveness of an MDS patient population for an FTI treatment. In some embodiments, the methods include analyzing a sample from the subject having MDS to determining that the subject has CXCL12-expressing MDS prior to administering the FTI to the subject. In some embodiments, the FTI is tipifarnib.

Provided herein are methods to treat CXCL12-expressing myelofibrosis in a subject including administering a therapeutically effective amount of an FTI to the subject having CXCL12-expressing myelofibrosis. Provided herein are also methods to predict the responsiveness of a subject having myelofibrosis for an FTI treatment, methods to select a myelofibrosis patient for an FTI treatment, methods to stratify myelofibrosis patients for an FTI treatment, and methods to increase the responsiveness of a myelofibrosis patient population for an FTI treatment. In some embodiments, the methods include analyzing a sample from the subject having myelofibrosis to determining that the subject has CXCL12-expressing myelofibrosis prior to administering the FTI to the subject. In some embodiments, the FTI is tipifarnib.

Provided herein are methods to treat CXCL12-expressing Waldenström's macroglobulinemia in a subject including administering a therapeutically effective amount of an FTI to the subject having CXCL12-expressing Waldenström's macroglobulinemia. Provided herein are also methods to predict the responsiveness of a subject having Waldenström's macroglobulinemia for an FTI treatment, methods to select a myelofibrosis patient for an FTI treatment, methods to stratify Waldenström's macroglobulinemia patients for an FTI treatment, and methods to increase the responsiveness of a Waldenström's macroglobulinemia patient population for an FTI treatment. In some embodiments, the methods include analyzing a sample from the subject having Waldenström's macroglobulinemia to determining that the subject has CXCL12-expressing Waldenström's macroglobulinemia prior to administering the FTI to the subject. In some embodiments, the FTI is tipifarnib.

Provided herein are methods to treat CXCL12-expressing sarcoma in a subject including administering a therapeutically effective amount of an FTI to the subject having CXCL12-expressing sarcoma. Provided herein are also methods to predict the responsiveness of a subject having sarcoma for an FTI treatment, methods to select a sarcoma patient for an FTI treatment, methods to stratify sarcoma patients for an FTI treatment, and methods to increase the responsiveness of a sarcoma patient population for an FTI treatment. In some embodiments, the methods include analyzing a sample from the subject having sarcoma to determining that the subject has CXCL12-expressing sarcoma prior to administering the FTI to the subject. In some embodiments, the FTI is tipifarnib.

In some embodiments, the sample from the subject can be a tumor biopsy or a body fluid sample. In some embodiments, the sample can be a whole blood sample, a partially purified blood sample, a peripheral blood sample, a serum sample, a cell sample or a lymph node sample. In some embodiments, the sample can be peripheral blood mononuclear cells (PBMC).

In some embodiments, the methods provided herein include determining the expression level of the CXCL12 gene in a sample from a subject having cancer, wherein the subject is determined to have CXCL12-expressing cancer if the expression level in the sample is higher than a reference level of the CXCL12. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CIVIL.

In some embodiments, the methods provided herein include determining the expression level of the CXCL12 gene in a sample from a subject having lymphoma, wherein the subject is determined to have CXCL12-expressing lymphoma if the expression level in the sample is higher than a reference level of the CXCL12. In specific embodiments, the lymphoma is an EBV associated lymphoma. In specific embodiments, the lymphoma is AITL. In specific embodiments, the lymphoma is CTCL.

In some embodiments, the methods provided herein include determining the expression level of the CXCL12 gene in a sample from a subject having PTCL, wherein the subject is determined to have CXCL12-expressing PTCL if the expression level in the sample is higher than a reference level of the CXCL12.

In some embodiments, the methods provided herein include determining the expression level of the CXCL12 gene in a sample from a subject having leukemia, wherein the subject is determined to have CXCL12-expressing leukemia if the expression level in the sample is higher than a reference level of the CXCL12. In specific embodiments, the leukemia is AML. In specific embodiments, the leukemia is T-ALL. In specific embodiments, the leukemia is CML.

In some embodiments, the methods provided herein include determining the expression level of the CXCL12 gene in a sample from a subject having MDS, wherein the subject is determined to have CXCL12-expressing MDS if the expression level in the sample is higher than a reference level of the CXCL12.

In some embodiments, the methods provided herein include determining the expression level of the CXCL12 gene in a sample from a subject having myelofibrosis, wherein the subject is determined to have CXCL12-expressing myelofibrosis if the expression level in the sample is higher than a reference level of the CXCL12.

In some embodiments, the methods provided herein include determining the expression level of the CXCL12 gene in a sample from a subject having Waldenström's macroglobulinemia, wherein the subject is determined to have CXCL12-expressing Waldenström's macroglobulinemia if the expression level in the sample is higher than a reference level of the CXCL12.

In some embodiments, the methods provided herein include determining the expression level of CXCL12 protein in a sample from a subject having cancer, and administering a therapeutically effective amount of an FTI to the subject if the CXCL12 protein expression level in the sample is higher than a reference level of CXCL12 protein. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CIVIL.

In some embodiments, the methods provided herein include determining the expression level of CXCL12 protein in a sample from a subject having lymphoma, and administering a therapeutically effective amount of an FTI to the subject if the CXCL12 protein expression level in the sample is higher than a reference level of CXCL12 protein. In specific embodiments, the lymphoma is an EBV associated lymphoma. In specific embodiments, the lymphoma is AITL. In specific embodiments, the lymphoma is CTCL.

In some embodiments, the methods provided herein include determining the expression level of CXCL12 protein in a sample from a subject having PTCL, and administering a therapeutically effective amount of an FTI to the subject if the CXCL12 protein expression level in the sample is higher than a reference level of CXCL12 protein.

In some embodiments, the methods provided herein include determining the expression level of CXCL12 protein in a sample from a subject having MDS, and administering a therapeutically effective amount of an FTI to the subject if the CXCL12 protein expression level in the sample is higher than a reference level of CXCL12 protein.

In some embodiments, the methods provided herein include determining the expression level of CXCL12 protein in a sample from a subject having myelofibrosis, and administering a therapeutically effective amount of an FTI to the subject if the CXCL12 protein expression level in the sample is higher than a reference level of CXCL12 protein.

In some embodiments, the methods provided herein include determining the expression level of CXCL12 protein in a sample from a subject having Waldenström's macroglobulinemia, and administering a therapeutically effective amount of an FTI to the subject if the CXCL12 protein expression level in the sample is higher than a reference level of CXCL12 protein.

In some embodiments, the methods provided herein include determining the expression level of CXCL12 protein in a sample from a subject having leukemia, and administering a therapeutically effective amount of an FTI to the subject if the CXCL12 protein expression level in the sample is higher than a reference level of CXCL12 protein. In specific embodiments, the leukemia is AML. In specific embodiments, the leukemia is T-ALL. In specific embodiments, the leukemia is CIVIL.

In some embodiments, the methods provided herein include determining the expression level of KIR3DL2 protein in a sample from a subject having PTCL, and administering a therapeutically effective amount of an FTI to the subject if the KIR3DL2 protein expression level in the sample is lower than a reference level of KIR3DL2 protein. In certain embodiments, the KIR3DL2 protein expression is determined by IHC. In certain embodiments, the KIR3DL2 protein expression is determined by FACS.

In some embodiments, the methods provided herein include determining the proportion of cells expressing KIR3DL2 in a sample from a subject having PTCL, and administering a therapeutically effective amount of an FTI to the subject if the proportion of cells expressing KIR3DL2 in the sample is lower than a reference level.

In some embodiments, the methods provided herein include determining the expression level of KIR3DL2 mRNA in a sample from a subject having PTCL, and administering a therapeutically effective amount of an FTI to the subject if the KIR3DL2 mRNA expression level in the sample is lower than a reference level of KIR3DL2 mRNA.

In some embodiments, the methods provided herein include determining the level of serum circulating CXCL12 in a sample from a subject having cancer, and administering a therapeutically effective amount of an FTI to the subject if the serum circulating CXCL12 level in the sample is higher than a reference level of serum circulating CXCL12. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CML.

In some embodiments, the methods provided herein include determining the level of serum circulating CXCL12 in a sample from a subject having lymphoma, and administering a therapeutically effective amount of an FTI to the subject if the serum circulating CXCL12 level in the sample is higher than a reference level of serum circulating CXCL12. In specific embodiments, the lymphoma is an EBV associated lymphoma. In specific embodiments, the lymphoma is AITL. In specific embodiments, the lymphoma is CTCL.

In some embodiments, the methods provided herein include determining the level of serum circulating CXCL12 in a sample from a subject having PTCL, and administering a therapeutically effective amount of an FTI to the subject if the serum circulating CXCL12 level in the sample is higher than a reference level of serum circulating CXCL12.

In some embodiments, the methods provided herein include determining the level of serum circulating CXCL12 in a sample from a subject having leukemia, and administering a therapeutically effective amount of an FTI to the subject if the serum circulating CXCL12 level in the sample is higher than a reference level of serum circulating CXCL12. In specific embodiments, the leukemia is AML. In specific embodiments, the leukemia is T-ALL. In specific embodiments, the leukemia is CIVIL.

In some embodiments, the methods provided herein include determining the level of serum circulating CXCL12 in a sample from a subject having MDS, and administering a therapeutically effective amount of an FTI to the subject if the serum circulating CXCL12 level in the sample is higher than a reference level of serum circulating CXCL12.

In some embodiments, the methods provided herein include determining the level of serum circulating CXCL12 in a sample from a subject having myelofibrosis, and administering a therapeutically effective amount of an FTI to the subject if the serum circulating CXCL12 level in the sample is higher than a reference level of serum circulating CXCL12.

In some embodiments, the methods provided herein include determining the level of serum circulating CXCL12 in a sample from a subject having Waldenström's macroglobulinemia, and administering a therapeutically effective amount of an FTI to the subject if the serum circulating CXCL12 level in the sample is higher than a reference level of serum circulating CXCL12.

In some embodiments, the methods provided herein further include determining the expression level of the CXCR4 gene in the sample from the subject having cancer, and the ratio of the expression level of a CXCL12 gene to that of the CXCR4 gene, wherein the subject is determined to have a high CXCL12/CXCR4 expression ratio if the ratio is higher than a reference ratio. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CML.

In some embodiments, the methods provided herein further include determining the expression level of the CXCR4 gene in the sample from the subject having lymphoma, and the ratio of the expression level of a CXCL12 gene to that of the CXCR4 gene, wherein the subject is determined to have a high CXCL12/CXCR4 expression ratio if the ratio is higher than a reference ratio. In specific embodiments, the lymphoma is an EBV associated lymphoma. In specific embodiments, the lymphoma is AITL. In specific embodiments, the lymphoma is CTCL.

In some embodiments, the methods provided herein further include determining the expression level of the CXCR4 gene in the sample from the subject having PTCL, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein further include determining the expression level of the CXCR4 gene in the sample from the subject having leukemia, and the ratio of the expression level of a CXCL12 gene to that of the CXCR4 gene, wherein the subject is determined to have a high CXCL12/CXCR4 expression ratio if the ratio is higher than a reference ratio. In specific embodiments, the leukemia is AML. In specific embodiments, the leukemia is T-ALL. In specific embodiments, the leukemia is CML.

In some embodiments, the methods provided herein further include determining the expression level of the CXCR4 gene in the sample from the subject having MDS, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein further include determining the expression level of the CXCR4 gene in the sample from the subject having myelofibrosis, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein further include determining the expression level of the CXCR4 gene in the sample from the subject having Waldenström's macroglobulinemia, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein further include determining the expression level of the CXCR4 gene in the sample from the subject having sarcoma, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein include determining the mRNA level of a gene in a sample from a subject having cancer. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In specific embodiments, the cancer is leukemia. In specific embodiments, the leukemia is AML. In specific embodiments, the leukemia is T-ALL. In specific embodiments, the leukemia is CML. In some embodiments, the methods provided herein include determining the mRNA level of a gene in a sample from a subject having lymphoma. In specific embodiments, the lymphoma is an EBV associated lymphoma. In specific embodiments, the lymphoma is AITL. In specific embodiments, the lymphoma is CTCL. In some embodiments, the methods provided herein include determining the mRNA level of a gene in a sample from a subject having PTCL. In some embodiments, the methods provided herein include determining the mRNA level of a gene in a sample from a subject having MDS. In some embodiments, the methods provided herein include determining the mRNA level of a gene in a sample from a subject having myelofibrosis. In some embodiments, the methods provided herein include determining the mRNA level of a gene in a sample from a subject having Waldenström's macroglobulinemia. In some embodiments, the mRNA level of the gene is determined by Polymerase Chain Reaction (PCR), qPCR, qRT-PCR, RNA-seq, microarray analysis, SAGE, MassARRAY technique, next-generation sequencing, or FISH.

In some embodiments, the methods provided herein include determining the protein level of a gene in a sample from a subject having cancer. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In specific embodiments, the cancer is leukemia. In specific embodiments, the leukemia is AML. In specific embodiments, the leukemia is T-ALL. In specific embodiments, the leukemia is CML. In some embodiments, the methods provided herein include determining the protein level of a gene in a sample from a subject having lymphoma. In specific embodiments, the lymphoma is an EBV associated lymphoma. In specific embodiments, the lymphoma is AITL. In specific embodiments, the lymphoma is CTCL. In some embodiments, the methods provided herein include determining the protein level of a gene in a sample from a subject having PTCL. In some embodiments, the methods provided herein include determining the protein level of a gene in a sample from a subject having MDS. In some embodiments, the methods provided herein include determining the protein level of a gene in a sample from a subject having myelofibrosis. In some embodiments, the methods provided herein include determining the protein level of a gene in a sample from a subject having Waldenström's macroglobulinemia. In some embodiments, the protein level of the gene can be determined by an immunohistochemistry (IHC) assay, an immunoblotting (IB) assay, an immunofluorescence (IF) assay, flow cytometry (FACS), or an Enzyme-Linked Immunosorbent Assay (ELISA). The IHC assay can be H&E staining.

In some embodiments, the methods provided herein include determining the ratio of CXCL12 expression to CXCR4 expression in the sample from the subject having cancer to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CIVIL.

In some embodiments, the methods provided herein include determining the ratio of CXCL12 expression to CXCR4 expression in the sample from the subject having lymphoma to be higher than a reference ratio. In some embodiments, the reference ratio can be 1/10, 1/9/, 1/8/, 1/7, 1/6, 1/5, 1/4, 1/3, 1/2, 1, 2, 3, 4, 5, 6, 7, 8, 9, 10, or 20. In specific embodiments, the lymphoma is an EBV associated lymphoma. In specific embodiments, the lymphoma is AITL. In specific embodiments, the lymphoma is CTCL.

In some embodiments, the methods provided herein include determining the ratio of CXCL12 expression to CXCR4 expression in the sample from the subject having PTCL to be higher than a reference ratio. In some embodiments, the reference ratio can be 1/10, 1/9/, 1/8/, 1/7, 1/6, 1/5, 1/4, 1/3, 1/2, 1, 2, 3, 4, 5, 6, 7, 8, 9, 10, or 20.

In some embodiments, the methods provided herein include determining the ratio of CXCL12 expression to CXCR4 expression in the sample from the subject having leukemia to be higher than a reference ratio. In some embodiments, the reference ratio can be 1/10, 1/9/, 1/8/, 1/7, 1/6, 1/5, 1/4, 1/3, 1/2, 1, 2, 3, 4, 5, 6, 7, 8, 9, 10, or 20. In specific embodiments, the leukemia is AML. In specific embodiments, the leukemia is T-ALL. In specific embodiments, the leukemia is CML.

In some embodiments, the methods provided herein include determining the ratio of CXCL12 expression to CXCR4 expression in the sample from the subject having MDS to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20.

In some embodiments, the methods provided herein include determining the ratio of CXCL12 expression to CXCR4 expression in the sample from the subject having myelofibrosis to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20.

In some embodiments, the methods provided herein include determining the ratio of CXCL12 expression to CXCR4 expression in the sample from the subject having Waldenström's macorglobulinemia to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20.

In some embodiments, the methods provided herein include determining the level of CXCL12 expression in a sample from a subject having cancer. In some embodiments, the methods provided herein include administering a therapeutically effective amount of an FTI to a subject having cancer if the level of a CXCL12 expression in a sample from the subject is higher than a reference level. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CML.

In some embodiments, the methods provided herein further include determining the level of CXCR4 expression in the sample from a subject having cancer. In some embodiments, the methods provided herein include administering a therapeutically effective amount of an FTI to a subject having cancer if the level of CXCR4 expression in a sample from the subject is lower than a reference level.

In some embodiments, the methods provided herein further include determining the ratio of the level of a CXCL12 expression to CXCR4 expression in the sample from a subject having cancer. In some embodiments, the methods provided herein include administering a therapeutically effective amount of an FTI to a subject having cancer if the ratio of the level of a CXCL12 expression to CXCR4 expression in a sample from the subject is higher than a reference ratio.

In some embodiments, the methods provided herein include determining the level of CXCL12 expression in a sample from a subject having lymphoma. In some embodiments, the methods provided herein include administering a therapeutically effective amount of an FTI to a subject having lymphoma if the level of a CXCL12 expression in a sample from the subject is higher than a reference level. In specific embodiments, the lymphoma is an EBV associated lymphoma. In specific embodiments, the lymphoma is AITL. In specific embodiments, the lymphoma is CTCL.

In some embodiments, the methods provided herein further include determining the level of CXCR4 expression in the sample from a subject having lymphoma. In some embodiments, the methods provided herein include administering a therapeutically effective amount of an FTI to a subject having lymphoma if the level of CXCR4 expression in a sample from the subject is lower than a reference level.

In some embodiments, the methods provided herein further include determining the ratio of the level of a CXCL12 expression to CXCR4 expression in the sample from a subject having lymphoma. In some embodiments, the methods provided herein include administering a therapeutically effective amount of an FTI to a subject having lymphoma if the ratio of the level of a CXCL12 expression to CXCR4 expression in a sample from the subject is higher than a reference ratio.

In some embodiments, the methods provided herein include determining the level of CXCL12 expression in a sample from a subject having PTCL. In some embodiments, the methods provided herein include administering a therapeutically effective amount of an FTI to a subject having PTCL if the level of a CXCL12 expression in a sample from the subject is higher than a reference level.

In some embodiments, the methods provided herein further include determining the level of CXCR4 expression in the sample from a subject having PTCL. In some embodiments, the methods provided herein include administering a therapeutically effective amount of an FTI to a subject having PTCL if the level of CXCR4 expression in a sample from the subject is lower than a reference level.

In some embodiments, the methods provided herein further include determining the ratio of the level of a CXCL12 expression to CXCR4 expression in the sample from a subject having PTCL. In some embodiments, the methods provided herein include administering a therapeutically effective amount of an FTI to a subject having PTCL if the ratio of the level of a CXCL12 expression to CXCR4 expression in a sample from the subject is higher than a reference ratio.

In some embodiments, the methods provided herein include determining the level of CXCL12 expression in a sample from a subject having leukemia. In some embodiments, the methods provided herein include administering a therapeutically effective amount of an FTI to a subject having leukemia if the level of a CXCL12 expression in a sample from the subject is higher than a reference level.

In some embodiments, the methods provided herein further include determining the level of CXCR4 expression in the sample from a subject having leukemia. In some embodiments, the methods provided herein include administering a therapeutically effective amount of an FTI to a subject having leukemia if the level of CXCR4 expression in a sample from the subject is lower than a reference level.

In some embodiments, the methods provided herein further include determining the ratio of the level of a CXCL12 expression to CXCR4 expression in the sample from a subject having leukemia. In some embodiments, the methods provided herein include administering a therapeutically effective amount of an FTI to a subject having leukemia if the ratio of the level of a CXCL12 expression to CXCR4 expression in a sample from the subject is higher than a reference ratio.

In some embodiments, the methods provided herein include determining the level of CXCL12 expression in a sample from a subject having MDS. In some embodiments, the methods provided herein include administering a therapeutically effective amount of an FTI to a subject having MDS if the level of a CXCL12 expression in a sample from the subject is higher than a reference level.

In some embodiments, the methods provided herein further include determining the level of CXCR4 expression in the sample from a subject having MDS. In some embodiments, the methods provided herein include administering a therapeutically effective amount of an FTI to a subject having MDS if the level of CXCR4 expression in a sample from the subject is lower than a reference level.

In some embodiments, the methods provided herein further include determining the ratio of the level of a CXCL12 expression to CXCR4 expression in the sample from a subject having MDS. In some embodiments, the methods provided herein include administering a therapeutically effective amount of an FTI to a subject having MDS if the ratio of the level of a CXCL12 expression to CXCR4 expression in a sample from the subject is higher than a reference ratio.

In some embodiments, the methods provided herein include determining the level of CXCL12 expression in a sample from a subject having myelofibrosis. In some embodiments, the methods provided herein include administering a therapeutically effective amount of an FTI to a subject having myelofibrosis if the level of a CXCL12 expression in a sample from the subject is higher than a reference level.

In some embodiments, the methods provided herein further include determining the level of CXCR4 expression in the sample from a subject having myelofibrosis. In some embodiments, the methods provided herein include administering a therapeutically effective amount of an FTI to a subject having myelofibrosis if the level of CXCR4 expression in a sample from the subject is lower than a reference level.

In some embodiments, the methods provided herein further include determining the ratio of the level of a CXCL12 expression to CXCR4 expression in the sample from a subject having myelofibrosis. In some embodiments, the methods provided herein include administering a therapeutically effective amount of an FTI to a subject having myelofibrosis if the ratio of the level of a CXCL12 expression to CXCR4 expression in a sample from the subject is higher than a reference ratio.

In some embodiments, the methods provided herein include determining the level of CXCL12 expression in a sample from a subject having Waldenström's macroglobulinemia. In some embodiments, the methods provided herein include administering a therapeutically effective amount of an FTI to a subject having Waldenström's macroglobulinemia if the level of a CXCL12 expression in a sample from the subject is higher than a reference level.

In some embodiments, the methods provided herein further include determining the level of CXCR4 expression in the sample from a subject having Waldenström's macroglobulinemia. In some embodiments, the methods provided herein include administering a therapeutically effective amount of an FTI to a subject having Waldenström's macroglobulinemia if the level of CXCR4 expression in a sample from the subject is lower than a reference level.

In some embodiments, the methods provided herein further include determining the ratio of the level of a CXCL12 expression to CXCR4 expression in the sample from a subject having Waldenström's macroglobulinemia. In some embodiments, the methods provided herein include administering a therapeutically effective amount of an FTI to a subject having Waldenström's macroglobulinemia if the ratio of the level of a CXCL12 expression to CXCR4 expression in a sample from the subject is higher than a reference ratio.

In some embodiments, the methods provided herein include analyzing expression levels in a sample from a subject by RT-PCR, microarray, Cytometric Bead Array, ELISA or Intracellular cytokine staining (ICS). In some embodiments, the sample is a serum sample.

In some embodiments, the methods provided herein to treat CXCL12-expressing lymphoma in a subject with an FTI, methods to predict the responsiveness of a subject having lymphoma for an FTI treatment, methods to select a lymphoma patient for an FTI treatment, methods to stratify lymphoma patients for an FTI treatment, and methods to increase the responsiveness of a lymphoma patient population for an FTI treatment further include determining the expression level of an AITL marker selected from the group consisting of CXCL13 and PD-1, in a sample from a subject having lymphoma, wherein if the expression level of the additional gene in the sample is higher than a reference expression level, the subject is predicted to be likely responsive to an FTI treatment, or is administered an therapeutically effective amount of an FTI.

In some embodiments, the methods provided herein further include determining the single nucleotide variant (SNV) status of CXCL12 in a sample from a subject having lymphoma. In some embodiments, a subject having lymphoma is predicted to be likely responsive to an FTI treatment, or is administered a therapeutically effective amount of an FTI if the sample does not have the rs2839695 SNV of CXCL12 (Sequence Variant Nomenclature—Human Genome Variation Society: NC_000010.10: g.44873849A>G, NC_000010.11:g.44378401A>G, NG_016861.1:g.11697T>C, NM_000609.6: c.266+236T>C, NM_001033886.2: c.266+236T>C, NM_001178134.1:c.266+236T>C, NM_001277990.1: c.109+2432T>C, NM_199168.3:c.*232T>C, XR_001747171.1:n.331+236T>C, XR_001747172.1: n.331+236T>C, XR_001747173.1:n.331+236T>C, XR_001747174.1:n.331+236T>C. Previously described rs17511729, rs17881270 have merged into rs2839695).

In some embodiments, a subject having lymphoma is predicted to be likely responsive to an FTI treatment, or is administered a therapeutically effective amount of an FTI if the sample does not have an SNV at position 44873186 (HGVS: NC_000010.10:g. 44873186C>T) of the 3' UTR of CXCL12. In some embodiments, a subject having leukemia is predicted to be likely responsive to an FTI treatment, or is administered a therapeutically effective amount of an FTI if the sample does not have an SNV at position 44866733 (HGVS: NC_000010.10:g. 44866733C>G) of the 3' UTR of CXCL12.

In some embodiments, a subject having lymphoma is predicted to be likely responsive to an FTI treatment, or is administered a therapeutically effective amount of an FTI if the sample does not have an SNV in the 3' UTR of CXCL12.

In some embodiments, a subject having lymphoma is predicted to be likely responsive to an FTI treatment, or is administered a therapeutically effective amount of an FTI if the sample does not have a SNV in the CXCL12 gene that results in low CXCL12 expression or the expression of an inactive CXCL12 protein. In specific embodiments, the lymphoma is an EBV associated lymphoma.

In some embodiments, the methods provided herein further include determining the SNV status of CXCL12 in a sample from a subject having leukemia. In some embodiments, a subject having leukemia is predicted to be likely responsive to an FTI treatment, or is administered a therapeutically effective amount of an FTI if the sample does not have the rs2839695 SNV of CXCL12. In some embodiments, a subject having leukemia is predicted to be likely responsive to an FTI treatment, or is administered a therapeutically effective amount of an FTI if the sample does not have an SNV at position 44873186 of the 3' UTR of CXCL12. In some embodiments, a subject having leukemia is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of CXCL12 in a sample from a subject having PTCL. In some embodiments, a subject having PTCL is predicted to be likely responsive to an FTI treatment, or is administered a therapeutically effective amount of an FTI if the sample does not have the rs2839695 SNV of CXCL12. In some embodiments, a subject having PTCL is predicted to be likely responsive to an FTI treatment, or is administered a therapeutically effective amount of an FTI if the sample does not have an SNV at position 44873186 of the 3' UTR of CXCL12. In some embodiments, a subject having PTCL is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of CXCL12 in a sample from a subject having MDS. In some embodiments, a subject having MDS is predicted to be likely responsive to an FTI treatment, or is administered a therapeutically effective amount of an FTI if the sample does not have the rs2839695 SNV of CXCL12. In some embodiments, a subject having MDS is predicted to be likely responsive to an FTI treatment, or is administered a therapeutically effective amount of an FTI if the sample does not have an SNV at position 44873186 of the 3' UTR of CXCL12. In some embodiments, a subject having MDS is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of CXCL12 in a sample from a subject having myelofibrosis. In some embodiments, a subject having myelofibrosis is predicted to be likely responsive to an FTI treatment, or is administered a therapeutically effective amount of an FTI if the sample does not have the rs2839695 SNV of CXCL12. In some embodiments, a subject having myelofibrosis is predicted to be likely responsive to an FTI treatment, or is administered a therapeutically effective amount of an FTI if the sample does not have an SNV at position 44873186 of the 3' UTR of CXCL12. In some embodiments, a subject having myelofibrosis is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of CXCL12 in a sample from a subject having Waldenström's macroglobulinemia. In some embodiments, a subject having Waldenström's macroglobulinemia is predicted to be likely responsive to an FTI treatment, or is administered a therapeutically effective amount of an FTI if the sample does not have the rs2839695 SNV of CXCL12. In some embodiments, a subject having Waldenström's macroglobulinemia is predicted to be likely responsive to an FTI treatment, or is administered a therapeutically effective amount of an FTI if the sample does not have an SNV at position 44873186 of the 3' UTR of CXCL12. In some embodiments, a subject having Waldenström's macroglobulinemia is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of SIK3 in a sample from a subject having cancer. In some embodiments, a subject having cancer is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having cancer is predicted to be likely responsive to an FTI treatment, or is administered a therapeutically effective amount of an FTI if the sample has a SIK3 SNV. In specific embodiments, the SIK3 SNV is N559H. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is leukemia.

In some embodiments, the methods provided herein further include determining the SNV status of SIK3 in a sample from a subject having lymphoma. In some embodiments, a subject having lymphoma is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having lymphoma is predicted to be likely responsive to an FTI treatment, or is administered a therapeutically effective amount of an FTI if the sample has a SIK3 SNV. In specific embodiments, the SIK3 SNV is N559H. In specific embodiments, the lymphoma is an EBV associated lymphoma.

In some embodiments, the methods provided herein further include determining the SNV status of SIK3 in a sample from a subject having PTCL. In some embodiments, a subject having PTCL is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having PTCL is predicted to be likely responsive to an FTI treatment, or is administered a therapeutically effective amount of an FTI if the sample has a SIK3 SNV. In specific embodiments, the SIK3 SNV is N559H.

In some embodiments, the methods provided herein further include determining the SNV status of SIK3 in a sample from a subject having PTCL. In some embodiments, a subject having PTCL is predicted to be likely responsive to a mitotic inhibitor, or is administered a therapeutically effective amount of a mitotic inhibitor if the sample has a SIK3 gene variant. In some embodiments, the mitotic inhibitor is an Aurora Kinase inhibitor. In some embodiments, the mitotic inhibitor is Alisertib. In some embodiments, the mitotic inhibitor is a PLK-1 inhibitor. In some embodiments, the mitotic inhibitor is Volasertib.

In some embodiments, the methods provided herein further include determining the SNV status of SIK3 in a sample from a subject having MDS. In some embodiments, a subject having MDS is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having MDS is predicted to be likely responsive to an FTI treatment, or is administered a therapeutically effective amount of an FTI if the sample has a SIK3 SNV. In specific embodiments, the SIK3 SNV is N559H.

In some embodiments, the methods provided herein further include determining the SNV status of SIK3 in a sample from a subject having myelofibrosis. In some embodiments, a subject having myelofibrosis is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having myelofibrosis is predicted to be likely responsive to an FTI treatment, or is administered a therapeutically effective amount of an FTI if the sample has a SIK3 SNV. In specific embodiments, the SIK3 SNV is N559H.

In some embodiments, the methods provided herein further include determining the SNV status of SIK3 in a sample from a subject having Waldenström's macroglobulinemia. In some embodiments, a subject having Waldenström's macroglobulinemia is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having Waldenström's macroglobulinemia is predicted to be likely responsive to an FTI treatment, or is administered a therapeutically effective amount of an FTI if the sample has a SIK3 SNV. In specific embodiments, the SIK3 SNV is N559H.

In some embodiments, the methods provided herein further include determining the SNV status of CENPF in a sample from a subject having cancer. In some embodiments, a subject having cancer is predicted to be likely responsive to an FTI treatment, or is administered a therapeutically effective amount of an FTI if the sample has the R2729Q gene variant. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is leukemia.

In some embodiments, the methods provided herein further include determining the SNV status of CENPF in a sample from a subject having lymphoma. In some embodiments, a subject having lymphoma is predicted to be likely responsive to an FTI treatment, or is administered a therapeutically effective amount of an FTI if the sample has the R2729Q gene variant. In specific embodiments, the lymphoma is an EBV associated lymphoma.

In some embodiments, the methods provided herein further include determining the SNV status of CENPF in a sample from a subject having PTCL. In some embodiments, a subject having PTCL is predicted to be likely responsive to an FTI treatment, or is administered a therapeutically effective amount of an FTI if the sample has the R2729Q gene variant.

In some embodiments, the methods provided herein further include determining the SNV status of CENPF in a sample from a subject having PTCL. In some embodiments, a subject having PTCL is predicted to be likely responsive to a mitotic inhibitor, or is administered a therapeutically effective amount of a mitotic inhibitor if the sample has the R2729Q gene variant. In some embodiments, the mitotic inhibitor is an Aurora Kinase inhibitor. In some embodiments, the mitotic inhibitor is Alisertib. In some embodiments, the mitotic inhibitor is a PLK-1 inhibitor. In some embodiments, the mitotic inhibitor is Volasertib.

In some embodiments, the methods provided herein further include determining the SNV status of CENPF in a sample from a subject having MDS. In some embodiments, a subject having MDS is predicted to be likely responsive to an FTI treatment, or is administered a therapeutically effective amount of an FTI if the sample has the R2729Q gene variant.

In some embodiments, the methods provided herein further include determining the SNV status of CENPF in a sample from a subject having myelofibrosis. In some embodiments, a subject having myelofibrosis is predicted to be likely responsive to an FTI treatment, or is administered a therapeutically effective amount of an FTI if the sample has the R2729Q gene variant.

In some embodiments, the methods provided herein further include determining the SNV status of CENPF in a sample from a subject having Waldenström's macroglobulinemia. In some embodiments, a subject having Waldenström's macroglobulinemia is predicted to be likely responsive to an FTI treatment, or is administered a therapeutically effective amount of an FTI if the sample has the R2729Q gene variant.

In some embodiments, the FTI is selected from the group consisting of tipifarnib, lonafarnib, CP-609,754, BMS-214662, L778123, L744823, L739749, R208176, AZD3409 and FTI-277. In some embodiments, the FTI is administered at a dose of 1-1000 mg/kg body weight. In some embodiments, the FTI is tipifarnib. In some embodiments, an FTI is administered at a dose of 200-1200 mg twice a day ("b.i.d."). In some embodiments, an FTI is administered at a dose of 600 mg twice a day. In some embodiments, an FTI is administered at a dose of 900 mg twice a day. In some embodiments, an FTI is administered at a dose of 1200 mg twice a day. In some embodiments, an FTI is administered at a dose of 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, or 1200 mg twice a day. In some embodiments, an FTI is administered daily for a period of one to seven days. In some embodiments, an FTI is administered in alternate weeks. In some embodiments, an FTI is administered on days 1-7 and 15-21 of a 28-day treatment cycle. In some embodiments, the treatment period can continue for up to 12 months. In some embodiments, tipifarnib is administered orally at a dose of 900 mg twice a day on days 1-7 and 15-21 of a 28-day treatment cycle.

In some embodiments, an FTI is administered before, during, or after irradiation. In some embodiments, the methods provided herein also include administering a therapeutically effective amount of a secondary active agent or a support care therapy to the subject. In some embodiments, the secondary active agent is a DNA-hypomethylating agent, a therapeutic antibody that specifically binds to a cancer antigen, a hematopoietic growth factor, cytokine, anti-cancer agent, antibiotic, cox-2 inhibitor, immunomodulatory agent, anti-thymocyte globulin, immunosuppressive agent, corticosteroid or a pharmacologically derivative thereof. In some embodiments, the secondary active agent is a DNA-hypomethylating agent, such as azacitidine or decitabine.

In some embodiments, the FTI for use in the compositions and methods provided herein is tipifarnib.

DETAILED DESCRIPTION

Figure 1:
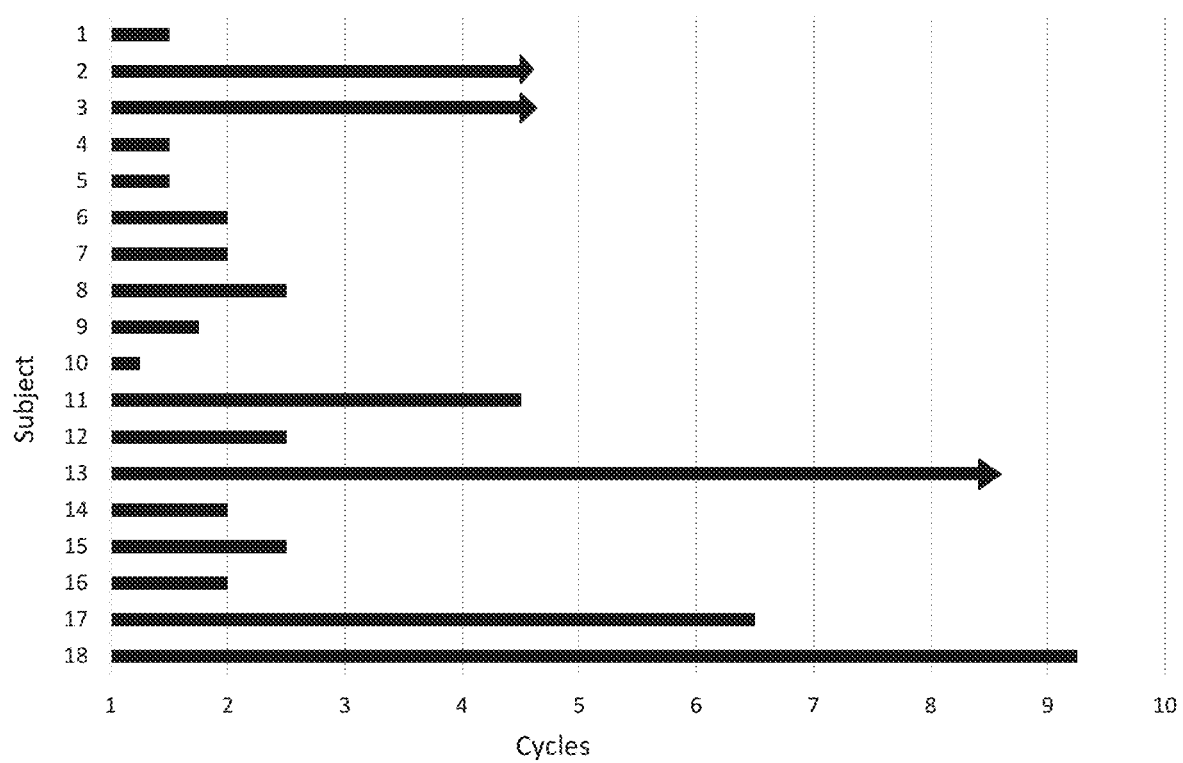
FIG. 1. Number of cycles of treatment received by the subjects in the PTCL tipifarnib clinical study. Arrows indicate ongoing treatment.

As used herein, the articles "a," "an," and "the" refer to one or to more than one of the grammatical object of the article. By way of example, a sample refers to one sample or two or more samples.

As used herein, the term "subject" refers to a mammal. A subject can be a human or a non-human mammal such as a dog, cat, bovid, equine, mouse, rat, rabbit, or transgenic species thereof. The subject can be a patient, a cancer patient, or a PTCL cancer patient.

As used herein, the term "sample" refers to a material or mixture of materials containing one or more components of interest. A sample from a subject refers to a sample obtained from the subject, including samples of biological tissue or fluid origin, obtained, reached, or collected in vivo or in situ. A sample can be obtained from a region of a subject containing precancerous or cancer cells or tissues. Such samples can be, but are not limited to, organs, tissues, fractions and cells isolated from a mammal. Exemplary samples include lymph node, whole blood, partially purified blood, serum, bone marrow, and peripheral blood mononuclear cells ("PBMC"). A sample also can be a tissue biopsy. Exemplary samples also include cell lysate, a cell culture, a cell line, a tissue, oral tissue, gastrointestinal tissue, an organ, an organelle, a biological fluid, a blood sample, a urine sample, a skin sample, and the like.

As used herein, the term "analyzing" a sample refers to carrying that an art-recognized assay to make an assessment regarding a particular property or characteristic of the sample. The property or characteristic of the sample can be, for example, the type of the cells in the sample, or the expression level of a gene in the sample.

As used herein, the terms "treat," "treating," and "treatment," when used in reference to a cancer patient, refer to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer.

As used herein, the term "administer," "administering," or "administration" refers to the act of delivering, or causing to be delivered, a compound or a pharmaceutical composition to the body of a subject by a method described herein or otherwise known in the art. Administering a compound or a pharmaceutical composition includes prescribing a compound or a pharmaceutical composition to be delivered into the body of a patient. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories.

As used herein, the term "therapeutically effective amount" of a compound when used in connection with a disease or disorder refers to an amount sufficient to provide a therapeutic benefit in the treatment or management of the disease or disorder or to delay or minimize one or more symptoms associated with the disease or disorder. A therapeutically effective amount of a compound means an amount of the compound that when used alone or in combination with other therapies, would provide a therapeutic benefit in the treatment or management of the disease or disorder. The term encompasses an amount that improves overall therapy, reduces or avoids symptoms, or enhances the therapeutic efficacy of another therapeutic agent. The term also refers to the amount of a compound that sufficiently elicits the biological or medical response of a biological molecule (e.g., a protein, enzyme, RNA, or DNA), cell, tissue, system, animal, or human, which is being sought by a researcher, veterinarian, medical doctor, or clinician.

As used herein, the term "express" or "expression" when used in connection with a gene refers to the process by which the information carried by the gene becomes manifest as the phenotype, including transcription of the gene to a messenger RNA (mRNA), the subsequent translation of the mRNA molecule to a polypeptide chain and its assembly into the ultimate protein.

As used herein, the term "expression level" of a gene refers to the amount or accumulation of the expression product of the gene, such as, for example, the amount of a RNA product of the gene (the RNA level of the gene) or the amount of a protein product of the gene (the protein level of the gene). If the gene has more than one allele, the expression level of a gene refers to the total amount of accumulation of the expression product of all existing alleles for this gene, unless otherwise specified.

As used herein, the term "reference" when used in connection with a quantifiable value refers to a predetermined value that one can use to determine the significance of the value as measured in a sample.

As used herein, the term "reference expression level" refers to a predetermined expression level of a gene that one can use to determine the significance of the expression level of the gene in a cell or in a sample. A reference expression level of a gene can be the expression level of the gene in a reference cell determined by a person of ordinary skill in the art. For example, the reference expression level of a CXCL12 gene can be its average expression level in naive CD4+ T cells. Accordingly, one can determine the expression level CXCL12 gene, if higher than the average expression level of the gene in naive CD4+ T cells, indicates that the cell is CXCL12-expressing cell. A reference expression level of a gene can also be a cut-off value determined by a person of ordinary skill in the art through statistical analysis of the expression levels of the gene in various sample cell populations. For example, by analyzing the expression levels of a gene in sample cell populations having at least 50%, at least 60%, at least 70%, at least 80%, at least 90% cells known to express that gene, a person of ordinary skill in the art can determine a cut-off value as the reference expression level of the gene, which can be used to indicate the percentages of cells expressing the gene in a cell population with unknown constitution.

The term "reference ratio" as used herein in connection with the expression levels of two genes refers to a ratio predetermined by a person of ordinary skill in the art that can be used to determine the significance of the ratio of the levels of these two genes in a cell or in a sample. The reference ratio of the expression levels of two genes can be the ratio of expression levels of these two genes in a reference cell determined by a person of ordinary skill in the art. A reference ratio can also be a cut-off value determined by a person of ordinary skill in the art through statistical analysis of ratios of expression levels of the two genes in various sample cell populations.

As used herein, the term "responsiveness" or "responsive" when used in connection with a treatment refers to the effectiveness of the treatment in lessening or decreasing the symptoms of the disease being treated. For example, a cancer patient is responsive to an FTI treatment if the FTI treatment effectively inhibits the cancer growth, or arrests development of the cancer, causes regression of the cancer, or delays or minimizes one or more symptoms associated with the presence of the cancer in this patient.

The responsiveness to a particular treatment of a cancer patient can be characterized as a complete or partial response. "Complete response" or "CR" refers to an absence of clinically detectable disease with normalization of previously abnormal radiographic studies, lymph node, and cerebrospinal fluid (CSF) or abnormal monoclonal protein measurements. "Partial response," or "PR," refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions.

A person of ordinary skill in the art would understand that clinical standards used to define CR, PR, or other level of patient responsiveness to treatments can vary for different subtypes of cancer. For example, for hematopoietic cancers, patient being "responsive" to a particular treatment can be defined as patients who have a complete response (CR), a partial response (PR), or hematological improvement (HI) (Lancet et al., *Blood* 2:2 (2006)). HI can be defined as any lymph node blast count less than 5% or a reduction in lymph node blasts by at least half. On the other hand, patient being "not responsive" to a particular treatment can be defined as patients who have either progressive disease (PD) or stable disease (SD). Progressive disease (PD) can be defined as either >50% increase in lymph node or circulating blast % from baseline, or new appearance of circulating blasts (on at least 2 consecutive occasions). Stable disease (SD) can be defined as any response not meeting CR, PR, HI, or PD criteria.

As used herein, the term "selecting" and "selected" in reference to a patient (e.g., a PTCL patient or AML, patient) is used to mean that a particular patient is specifically chosen from a larger group of patients on the basis of (due to) the particular patient having a predetermined criteria or a set of predetermined criteria, e.g., the patient having a CXCL12/CXCL4 expression level ration greater than a reference ratio. Similarly, "selectively treating a patient" refers to providing treatment to a patient (e.g., a PTCL or AML, patient) that is specifically chosen from a larger group of patients on the basis of (due to) the particular patient having a predetermined criteria or a set of predetermined criteria, e.g., the patient having a CXCL12/CXCL4 expression level ration greater than a reference ratio. Similarly, "selectively administering" refers to administering a drug to a patient (e.g., a PTCL or AML patient) that is specifically chosen from a larger group of patients on the basis of (due to) the particular patient having a predetermined criteria or a set of predetermined criteria, e.g., the patient having a CXCL12/CXCL4 expression level ration greater than a reference ratio. By selecting, selectively treating and selectively administering, it is meant that a patient is delivered a personalized therapy for a disease or disorder, e.g., cancer (such as PTCL or AML), based on the patient's biology, rather than being delivered a standard treatment regimen based solely on having the disease or disorder (e.g., PTCL or AML).

As used herein, the term "likelihood" refers to the probability of an event. A subject is "likely" to be responsive to a particular treatment when a condition is met means that the probability of the subject to be responsive to a particular treatment is higher when the condition is met than when the condition is not met. The probability to be responsive to a particular treatment can be higher by, for example, 5%, 10%, 25%, 50%, 100%, 200%, or more in a subject who meets a particular condition compared to a subject who does not meet the condition. For example, a subject having PTCL is "likely" responsive to an FTI treatment when the subject has a high CXCL12/CXCR4 expression ratio means that the probability of a subject to be responsive to FTI treatment is 5%, 10%, 25%, 50%, 100%, 200%, or more higher in a subject who has a high CXCL12/CXCR4 expression ratio compared to a subject who has a low CXCL12/CXCR4 expression ratio.

CXCL12 (or Stroma Derived Factor 1) is a strong chemotactic agent for lymphocytes. During embryogenesis, CXCL12 directs the migration of hematopoietic cells from fetal liver to bone, and in adulthood, CXCL12 plays an important role in angiogenesis by recruiting endothelial progenitor cells through a CXCR4-dependent mechanism. CXCL12 is also expressed within the splenic red pulp and lymph node medullary cords. See Pitt et al., 2015, Cancer Cell 27:755-768 and Zhao et al., 2011, Proc. Natl. Acad. Sci. USA 108:337-342. An exemplary amino acid sequence and a corresponding encoding nucleic acid sequence of human CXCL12 may be found at GENBANK ACCESSION NOS.: NP_000600.1 and NM_000609.6, respectively.

CXCR4 (also known as fusin or CD184) is a receptor specific for CXCL12. An exemplary amino acid sequence and a corresponding encoding nucleic acid sequence of human CXCR4 may be found at GENBANK ACCESSION NOS.: NP_001008540.1 and NM_001008540.1, respectively.

KIR (Killer Cell Immunoglobulin-Like Receptor) molecules are transmembrane glycoproteins expressed by natural killer cells and certain subsets of T cells, and include, for example, KIR2DS2, KIR2DS5, KIR3DL1 and KIR3DL2. An exemplary amino acid sequence and a corresponding encoding nucleic acid sequence of human KIR3DL2 may be found at GENBANK ACCESSION NOS.: NP_001229796.1 and NM_001242867.1, respectively.

The tumor suppressor LKB1 acts through salt-inducible kinase 2 (SIK2) and SIK3 to promote nucleocytoplasmic trafficking of class IIa histone deacetylases. See Walkinshaw et al., 2013, J. Biol. Chem. 288:9345-9362. SIK3 is important for proper mitosis and downregulation of SIK3 results in delayed mitotic exit. SIK3 inhibition sensitizes cells to pharmacological inhibition of mitotic kinases, including Aurora A, Aurora B, and polo-like kinase 1. See Chen et al., 2014, Cell Death and Disease 5:e1177. An exemplary amino acid sequence and a corresponding encoding nucleic acid sequence of human SIK3 may be found at GENBANK ACCESSION NOS.: NP_001268678.1 and NM_001281749.1, respectively.

CENPF is a farnesylated protein that binds kinetochores. Localisation of CENPF to the nuclear envelope at G2/M, and to kinetochores in prometaphase is dependent on farnesyl transferase activity. Farnesyl transferase activity is also required for CENPF protein degradation after mitosis. See Hussein et al., 2002, J. Cell Sci. 115:3403-3414. An exemplary amino acid sequence and a corresponding encoding nucleic acid sequence of human CENPF may be found at GENBANK ACCESSION NOS.: NP_057427.3 and NM_016343.3, respectively.

Lymphoma is the most common blood cancer. The two main forms of lymphoma are Hodgkin's lymphoma, or HL, and Non-Hodgkin's lymphoma, or NHL. Lymphoma occurs when cells of the immune system called lymphocytes grow and multiply uncontrollably. Cancerous lymphocytes can travel to many parts of the body, including lymph node, spleen, blood, or other organs, and form tumors. The body has two main types of lymphocytes that can develop into lymphomas: B-cells and T-cells.

AML is a cancer of the myeloid line of blood cells. AML is characterized by the rapid growth of abnormal white blood cells that can build up in the bone marrow and interfere with the production of normal blood cells. AML is the most common acute leukemia affecting adults, and its incidence increases with age. AML accounts for roughly 1.2% of cancer deaths in the United States, and its incidence is generally expected to increase as the population ages. The AML symptoms are believed to relate to replacement of normal bone marrow with leukemic cells, which can cause a drop in red blood cells, platelets, and normal white blood cells. AML symptoms can include fatigue, shortness of breath, easy bruising and bleeding, and increased risk of infection. AML often progresses rapidly and is typically fatal within weeks or months if left untreated.

PTCL consists of a group of rare and usually aggressive (fast-growing) NHLs that develop from mature T-cells. PTCLs collectively account for about 5 to 10 percent of all NHL cases, corresponding to an annual incidence of approximately 5,000 patients per year in the U.S. By some estimates, the incidence of PTCL is growing significantly, and the increasing incidence may be attributable to an aging population.

PTCLs are sub-classified into various subtypes, including Anaplastic large cell lymphoma (ALCL), ALK positive; ALCL, ALK negative; Angioimmunoblastic T-cell lymphoma (AITL); Enteropathy-associated T-cell lymphoma; Extranodal natural killer (NK) T-cell lymphoma, nasal type; Hepatosplenic T-cell lymphoma; PTCL, not otherwise specified (NOS); and Subcutaneous panniculitis-like T-cell lymphoma. Each of these subtypes are typically considered to be separate diseases based on their distinct clinical differences. Most of these subtypes are rare; the three most common subtypes are PTCL NOS, AITL, and ALCL, and these collectively account for approximately 70 percent of all PTCL cases. In some embodiments herein, the PTCL is relapsed or refractory PTCL. In other embodiments, the PTCL is relapsed or refractory advanced PTCL.

AITL is characterized histologically by a tumor cell component and a non-tumor cell component. The tumor cell component comprises polymorphous medium-sized neoplastic cells derived from an unique T-cell subset located in lymph nodes germinal centers called follicular helper T cells (TFH). TFH express CXCL13, VEGF and angpt1. CXCL13 can induce the expression of CXCL12 in mesenchymal cells. VEGF and angiopoietin induce the formation of venules of endothelial cells that express CXCL12. The non-tumor cell component comprises prominent arborizing blood vessels, proliferation of follicular dendritic cells, and scattered EBV+ B-cell blasts. Visualization of arborizing blood vessels is a hallmark of the diagnosis of AITL. By visualizing the vessels (endothelial venules), CXCL12 expressing endothelial cells can be identified. Targeted loss of CXCL12 expression in vascular endothelial cells translates to loss of T cell tumors in lymph nodes, spleen and bone marrow (Pitt et al., 2015, "CXCL12-Producing Vascular Endothelial Niches Control Acute T Cell Leukemia Maintenance," Cancer Cell 27:755-768). These are the tumor locations not only for T-LL but also for AITL.

T cells can be separated into three major groups based on function: cytotoxic T cells, helper T cells (Th), and regulatory T cells (Tregs). Differential expression of markers on the cell surface, as well as their distinct cytokine secretion profiles, provide valuable clues to the diverse nature and function of T cells. For example, CD8+ cytotoxic T cells destroy infected target cells through the release of perforin, granzymes, and granulysin, whereas CD4+T helper cells have little cytotoxic activity and secrete cytokines that act on other leucocytes such as B cells, macrophages, eosinophils, or neutrophils to clear pathogens. Tregs suppress T-cell function by several mechanisms including binding to effector T-cell subsets and preventing secretion of their cytokines. Helper T cells can be further categorized into difference classes, including e.g., Th1, Th2, Th9, Th17, and Tfh cells. Differentiation of CD4+ T cells into Th1 and Th2 effector cells is largely controlled by the transcription factors TBX21 (T-Box Protein 21; T-bet) and GATA3 (GATA3), respectively. Both TBX21 and GATA3 are transcription factors that are master regulators of gene expression profiles in T helper (Th) cells, skewing Th polarization into Th1 and Th2 differentiation pathways, respectively. Thus, Th1 cells are characterized by high expression levels of TBX21 and the target genes activated by TBX21, and low expression levels of GATA3 and genes activated by GATA3. To the contrary, Th2 cells are characterized by high expression levels of GATA3 and the target genes activated by GATA3, and low expression levels of TBX21 and genes activated by TBX21.

PTCL and its subtypes (e.g. PTCL NOS) can be categorized based on Th1 or Th2 lineage derivation.

A. Methods

Provided herein are methods for selecting a subject having cancer, for example, a lymphoma, for example, PTCL, for treatment with a FTI. In some embodiments, the lymphoma is angioimmunoblastic T-cell lymphoma (AITL), PTCL not otherwise specified (PTCL-NOS), anaplastic large cell lymphoma (ALCL)-anaplastic lymphoma kinase (ALK) positive, ALCL-ALK negative, enteropathy-associated T-cell lymphoma, extranodal natural killer cell (NK) T-cell lymphoma-nasal type, hepatosplenic T-cell lymphoma, or subcutaneous panniculitis-like T-cell lymphoma. In certain embodiments, the lymphoma is AITL. In certain embodiments, the lymphoma is PTCL-NOS. In specific embodiments, the lymphoma is CTCL. In certain embodiments, the cancer is a leukemia. In specific embodiments, the leukemia is AML (e.g., newly diagnosed AML or relapsed or refractory AML). In specific embodiments, the leukemia is T-ALL. In specific embodiments, the leukemia is CML. The methods provided herein are based, in part, on the discovery that the patients having cancers with different gene expression respond differently to an FTI treatment, and that the clinical benefits of FTI is associated with the expression level of certain genes and gene variants in the cancer. For example, methods provided herein are based on the discovery that patients having a higher ratio of CXCL12 expression to CXCR4 expression are likely responsive to an FTI treatment, and selection of patient population having a cancer with a high CXCL12 to CXCR4 expression ratio for an FTI treatment can increase the overall response rate of the FTI treatment for that cancer. In some embodiments, the FTI is tipifarnib.

Accordingly, provided herein are methods for increasing the responsiveness of an FTI treatment for cancer by selectively treating cancer patients having specific gene expression patterns. Provided herein are also methods for cancer patient population selection for an FTI treatment. Provided herein are also methods of predicting responsiveness of a subject having cancer to an FTI treatment based on the gene expression pattern, wherein a subject is predicted to be likely response if the subject has that gene expression pattern.

In some embodiments, provided herein are methods to treat cancer in a subject, including administering a therapeutically effective amount of an FTI to the subject having cancer with a certain gene expression pattern. In some embodiments, the methods include analyzing a sample from the subject to determine that the subject has a cancer with that gene expression pattern.

In some embodiments, methods provided herein also include obtaining a sample from the subject. The sample used in the methods provided herein includes body fluids from a subject or a tumour biopsy from the subject.

In some embodiments, the sample used in the present methods includes a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy. In some embodiments, the sample is a lymph node biopsy. In some embodiments, the sample can be a frozen tissue sample. In some embodiments, the sample can be a formalin-fixed paraffin-embedded ("FFPE") tissue sample. In some embodiments, the sample can be a deparaffinised tissue section.

In some embodiments, the sample is a body fluid sample. Non-limiting examples of body fluids include blood (e.g., peripheral whole blood, peripheral blood), blood plasma, bone marrow, amniotic fluid, aqueous humor, bile, lymph, menses, serum, urine, cerebrospinal fluid surrounding the brain and the spinal cord, synovial fluid surrounding bone joints.

In some embodiments, the sample is a blood sample. The blood sample can be a whole blood sample, a partially purified blood sample, or a peripheral blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Sub-populations of white blood cells, e.g. mononuclear cells, NK cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10.0 mL.

In one embodiment, the sample is a bone marrow sample. Procedures to obtain a bone marrow sample are well known in the art, including but not limited to bone marrow biopsy and bone marrow aspiration. Bone marrow has a fluid portion and a more solid portion. In bone marrow biopsy, a sample of the solid portion is taken. In bone marrow aspiration, a sample of the fluid portion is taken. Bone marrow biopsy and bone marrow aspiration can be done at the same time and referred to as a bone marrow exam.

In certain embodiments, the sample used in the methods provided herein includes a plurality of cells. Such cells can include any type of cells, e.g., stem cells, blood cells (e.g., PBMCs), lymphocytes, NK cells, B cells, T cells, monocytes, granulocytes, immune cells, or tumor or cancer cells. Specific cell populations can be obtained using a combination of commercially available antibodies (e.g., Quest Diagnostic (San Juan Capistrano, Calif.); Dako (Denmark)). In certain embodiments, the sample used in the methods provided herein includes PBMCs.

In certain embodiments, the sample used in the methods provided herein includes a plurality of cells from the diseased tissue, for example, the PTCL or AML tumor sample from the subject. In some embodiments, the cells can be obtained from the tumor tissue, such as a tumor biopsy or a tumor explants. In certain embodiments, the number of cells used in the methods provided herein can range from a single cell to about $10^9$ cells. In some embodiments, the number of cells used in the methods provided herein is about $1\times10^4$, $5\times10^4$, $1\times10^5$, $5\times10^5$, $1\times10^6$, $5\times10^6$, $1\times10^7$, $5\times10^7$, $1\times10^8$, or $5\times10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

In some embodiments, the methods provided herein include determining the level of serum circulating CXCL12 in a sample from a subject having cancer, and administering a therapeutically effective amount of an FTI to the subject if the serum circulating CXCL12 level in the sample is higher than a reference level of serum circulating CXCL12. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CML.

In some embodiments, the methods provided herein include determining the level of serum circulating CXCL12 in a sample from a subject having lymphoma, and administering a therapeutically effective amount of an FTI to the subject if the serum circulating CXCL12 level in the sample is higher than a reference level of serum circulating CXCL12. In specific embodiments, the lymphoma is an EBV associated lymphoma. In some embodiments, the lymphoma is AITL, PTCL-NOS, ALCL-ALK positive, ALCL-ALK negative, enteropathy-associated T-cell lymphoma, extranodal natural killer cell (NK) T-cell lymphoma-nasal type, hepatosplenic T-cell lymphoma, or subcutaneous panniculitis-like T-cell lymphoma. In specific embodiments, the lymphoma is AITL. In other specific embodiments, the lymphoma is PTCL-NOS. In some embodiments, the methods provided herein include determining the level of serum circulating CXCL12 in a sample from a subject having PTCL, and administering a therapeutically effective amount of an FTI to the subject if the serum circulating CXCL12 level in the sample is higher than a reference level of serum circulating CXCL12.

In some embodiments, the methods provided herein include determining the level of serum circulating CXCL12 in a sample from a subject having AML, and administering a therapeutically effective amount of an FTI to the subject if the serum circulating CXCL12 level in the sample is higher than a reference level of serum circulating CXCL12. In some embodiments, the AML is newly diagnosed. In some embodiments, the subject is an elderly patient with poor-risk AML. In some embodiments, the AML is relapsed or refractory AML.

In some embodiments, the methods provided herein include determining the level of serum circulating CXCL12 in a sample from a subject having MDS, and administering a therapeutically effective amount of an FTI to the subject if the serum circulating CXCL12 level in the sample is higher than a reference level of serum circulating CXCL12.

In some embodiments, the methods provided herein include determining the level of serum circulating CXCL12 in a sample from a subject having myelofibrosis, and administering a therapeutically effective amount of an FTI to the subject if the serum circulating CXCL12 level in the sample is higher than a reference level of serum circulating CXCL12.

In some embodiments, the methods provided herein include determining the level of serum circulating CXCL12 in a sample from a subject having Waldenström's macroglobulinemia, and administering a therapeutically effective amount of an FTI to the subject if the serum circulating CXCL12 level in the sample is higher than a reference level of serum circulating CXCL12.

In some embodiments, the sample used in methods provided herein can be a whole blood sample, a partially purified blood sample, a peripheral blood sample, a serum sample, a cell sample or a lymph node sample. The sample can be a tissue biopsy or a tumor biopsy. In some embodiments, the sample is a lymph node biopsy from a subject having lymphoma, for example, PTCL or CTCL. In some embodiments, the sample is the PBMCs from a subject having lymphoma, for example, PTCL. In some embodiments, the sample is a lymph node or bone marrow biopsy from a subject having leukemia, for example, AML, T-ALL, or CML. In some embodiments, the sample is the PBMCs from a subject having leukemia, for example, AML, T-ALL or CML.

The sample can be a tumor biopsy, a blood sample, a lymph node sample, or any other sample disclosed herein. In some embodiments, the FTI is tipifarnib.

Provided herein are methods to treat CXCL12-expressing cancer in a subject including administering a therapeutically effective amount of an FTI to the subject having a CXCL12-expressing cancer. Provided herein are also methods to predict the responsiveness of a subject having cancer for an FTI treatment, methods to select a cancer patient for an FTI treatment, methods to stratify cancer patients for an FTI treatment, and methods to increase the responsiveness of a cancer patient population for an FTI treatment. In some embodiments, the methods include analyzing a sample from the subject having cancer to determining that the subject has CXCL12-expressing cancer prior to administering the FTI to the subject. In some embodiments, the FTI is tipifarnib. In specific embodiments, the cancer is nasopharyngeal carcinoma. In specific embodiments, the cancer is EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CIVIL.

Provided herein are methods to treat CXCL12-expressing lymphoma in a subject including administering a therapeutically effective amount of an FTI to the subject having a CXCL12-expressing lymphoma. Provided herein are also methods to predict the responsiveness of a subject having lymphoma for an FTI treatment, methods to select a lymphoma patient for an FTI treatment, methods to stratify lymphoma patients for an FTI treatment, and methods to increase the responsiveness of a lymphoma patient population for an FTI treatment. In some embodiments, the methods include analyzing a sample from the subject having lymphoma to determining that the subject has CXCL12-expressing lymphoma prior to administering the FTI to the subject. In some embodiments, the FTI is tipifarnib. In some embodiments, the lymphoma is AITL, PTCL-NOS, ALCL-ALK positive, ALCL-ALK negative, enteropathy-associated T-cell lymphoma, extranodal natural killer cell (NK) T-cell lymphoma-nasal type, hepatosplenic T-cell lymphoma, or subcutaneous panniculitis-like T-cell lymphoma. In specific embodiments, the lymphoma is an EBV associated lymphoma. In specific embodiments, the lymphoma is AITL. In specific embodiments, the lymphoma is PTCL-NOS. In specific embodiments, the lymphoma is CTCL.

Provided herein are methods to treat CXCL12-expressing leukemia in a subject including administering a therapeutically effective amount of an FTI to the subject having a CXCL12-expressing leukemia. Provided herein are also methods to predict the responsiveness of a subject having leukemia for an FTI treatment, methods to select a leukemia patient for an FTI treatment, methods to stratify leukemia patients for an FTI treatment, and methods to increase the responsiveness of a leukemia patient population for an FTI treatment. In some embodiments, the methods include analyzing a sample from the subject having leukemia to determining that the subject has CXCL12-expressing leukemia prior to administering the FTI to the subject. In some embodiments, the FTI is tipifarnib. In certain embodiments, the leukemia is AML. In specific embodiments, the AML is newly diagnosed. In specific embodiments, the subject is an elderly patient with poor-risk AML. In some embodiments, the AML is relapsed or refractory AML. In specific embodiments, the leukemia is T-ALL. In specific embodiments, the leukemia is CIVIL.

Provided herein are methods to treat CXCL12-expressing PTCL (e.g., AITL or PTCL-NOS) in a subject including administering a therapeutically effective amount of an FTI to the subject having a CXCL12-expressing PTCL. Provided herein are also methods to predict the responsiveness of a subject having PTCL (e.g., AITL or PTCL-NOS) for an FTI treatment, methods to select a PTCL patient for an FTI treatment, methods to stratify PTCL patients for an FTI treatment, and methods to increase the responsiveness of a PTCL patient population for an FTI treatment. In some embodiments, the methods include analyzing a sample from the subject having PTCL to determining that the subject has CXCL12-expressing PTCL prior to administering the FTI to the subject. In some embodiments, the FTI is tipifarnib.

Provided herein are methods to treat CXCL12-expressing myelodysplastic syndrome (MDS) in a subject including administering a therapeutically effective amount of an FTI to the subject having CXCL12-expressing MDS. Provided herein are also methods to predict the responsiveness of a subject having MDS for an FTI treatment, methods to select an MDS patient for an FTI treatment, methods to stratify MDS patients for an FTI treatment, and methods to increase the responsiveness of an MDS patient population for an FTI treatment. In some embodiments, the methods include analyzing a sample from the subject having MDS to determining that the subject has CXCL12-expressing MDS prior to administering the FTI to the subject. In some embodiments, the FTI is tipifarnib.

Provided herein are methods to treat CXCL12-expressing myelofibrosis in a subject including administering a therapeutically effective amount of an FTI to the subject having CXCL12-expressing myelofibrosis. Provided herein are also methods to predict the responsiveness of a subject having myelofibrosis for an FTI treatment, methods to select a myelofibrosis patient for an FTI treatment, methods to stratify myelofibrosis patients for an FTI treatment, and methods to increase the responsiveness of a myelofibrosis patient population for an FTI treatment. In some embodiments, the methods include analyzing a sample from the subject having myelofibrosis to determining that the subject has CXCL12-expressing myelofibrosis prior to administering the FTI to the subject. In some embodiments, the FTI is tipifarnib.

Provided herein are methods to treat CXCL12-expressing Waldenström's macroglobulinemia in a subject including administering a therapeutically effective amount of an FTI to the subject having CXCL12-expressing Waldenström's macroglobulinemia. Provided herein are also methods to predict the responsiveness of a subject having Waldenström's macroglobulinemia for an FTI treatment, methods to select a Waldenström's macroglobulinemia patient for an FTI treatment, methods to stratify Waldenström's macroglobulinemia patients for an FTI treatment, and methods to increase the responsiveness of a Waldenström's macroglobulinemia patient population for an FTI treatment. In some embodiments, the methods include analyzing a sample from the subject having Waldenström's macroglobulinemia to determining that the subject has CXCL12-expressing Waldenström's macroglobulinemia prior to administering the FTI to the subject. In some embodiments, the FTI is tipifarnib.

In some embodiments, the methods provided herein include determining the expression level of the CXCL12 gene in a sample from a subject having cancer, wherein the subject is determined to have CXCL12-expressing cancer if the expression level in the sample is higher than a reference level of the CXCL12. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is leukemia (e.g., AML).

In some embodiments, the methods provided herein include determining the expression level of the CXCL12 gene in a sample from a subject having lymphoma, wherein the subject is determined to have CXCL12-expressing lymphoma if the expression level in the sample is higher than a reference level of the CXCL12. In some embodiments, the lymphoma is AITL, PTCL-NOS, ALCL-ALK positive, ALCL-ALK negative, enteropathy-associated T-cell lymphoma, extranodal natural killer cell (NK) T-cell lymphoma-nasal type, hepatosplenic T-cell lymphoma, or subcutaneous panniculitis-like T-cell lymphoma. In specific embodiments, the lymphoma is an EBV associated lymphoma. In specific embodiments, the lymphoma is AITL. In some embodiments, the lymphoma is PTCL-NOS. In specific embodiments, the lymphoma is CTCL.

In some embodiments, the methods provided herein include determining the expression level of the CXCL12 gene in a sample from a subject having PTCL, wherein the subject is determined to have CXCL12-expressing PTCL if the expression level in the sample is higher than a reference level of the CXCL12.

In some embodiments, the methods provided herein include determining the expression level of the CXCL12 gene in a sample from a subject having leukemia, wherein the subject is determined to have CXCL12-expressing leukemia if the expression level in the sample is higher than a reference level of the CXCL12. In specific embodiments, the leukemia is AML. In some embodiments, the AML is newly diagnosed. In some embodiments, the subject is an elderly patient with poor-risk AML. In some embodiments, the AML is relapsed or refractory AML. In specific embodiments, the leukemia is T-ALL. In specific embodiments, the leukemia is CML.

In some embodiments, the methods provided herein include determining the expression level of the CXCL12 gene in a sample from a subject having MDS, wherein the subject is determined to have CXCL12-expressing MDS if the expression level in the sample is higher than a reference level of the CXCL12.

In some embodiments, the methods provided herein include determining the expression level of the CXCL12 gene in a sample from a subject having myelofibrosis, wherein the subject is determined to have CXCL12-expressing myelofibrosis if the expression level in the sample is higher than a reference level of the CXCL12.

In some embodiments, the methods provided herein include determining the expression level of the CXCL12 gene in a sample from a subject having Waldenström's macroglobulinemia, wherein the subject is determined to have CXCL12-expressing Waldenström's macroglobulinemia if the expression level in the sample is higher than a reference level of the CXCL12.

In some embodiments, the methods provided herein further include determining the expression level of the CXCR4 gene in the sample from the subject having cancer, and the ratio of the expression level of a CXCL12 gene to that of the CXCR4 gene, wherein the subject is determined to have a high CXCL12/CXCR4 expression ratio if the ratio is higher than a reference ratio. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CML.

In some embodiments, the methods provided herein further include determining the expression level of the CXCR4 gene in the sample from the subject having lymphoma, and the ratio of the expression level of a CXCL12 gene to that of the CXCR4 gene, wherein the subject is determined to have a high CXCL12/CXCR4 expression ratio if the ratio is higher than a reference ratio. In some embodiments, the lymphoma is AITL, PTCL-NOS, ALCL-ALK positive, ALCL-ALK negative, enteropathy-associated T-cell lymphoma, extranodal natural killer cell (NK) T-cell lymphoma-nasal type, hepatosplenic T-cell lymphoma, or subcutaneous panniculitis-like T-cell lymphoma. In specific embodiments, the lymphoma is an EBV associated lymphoma. In specific embodiments, the lymphoma is AITL. In some embodiments, the lymphoma is PTCL-NOS. In specific embodiments, the lymphoma is CTCL.

In some embodiments, the methods provided herein further include determining the expression level of the CXCR4 gene in the sample from the subject having PTCL, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein further include determining the expression level of the CXCR4 gene in the sample from the subject having leukemia, and the ratio of the expression level of a CXCL12 gene to that of the CXCR4 gene, wherein the subject is determined to have a high CXCL12/CXCR4 expression ratio if the ratio is higher than a reference ratio. In certain embodiments, the leukemia is AML. In specific embodiments, the AML is newly diagnosed. In specific embodiments, the subject is an elderly patient with poor-risk AML. In specific embodiments, the AML is relapsed or refractory AML. In specific embodiments, the leukemia is T-ALL. In specific embodiments, the leukemia is CIVIL.

In some embodiments, the methods provided herein further include determining the expression level of the CXCR4 gene in the sample from the subject having MDS, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein further include determining the expression level of the CXCR4 gene in the sample from the subject having myelofibrosis, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein further include determining the expression level of the CXCR4 gene in the sample from the subject having Waldenström's macroglobulinemia, and the ratio of the expression level of a CXCL12 gene to that of the CXCR4 gene, wherein the subject is determined to have a high CXCL12/CXCR4 expression ratio if the ratio is higher than a reference ratio.

In some embodiments, the methods provided herein include determining the ratio of CXCL12 expression to CXCR4 expression in the sample from the subject having cancer to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CIVIL.

In some embodiments, the methods provided herein include determining the ratio of CXCL12 expression to CXCR4 expression in the sample from the subject having lymphoma to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20. In some embodiments, the lymphoma is AITL, PTCL-NOS, ALCL-ALK positive, ALCL-ALK negative, enteropathy-associated T-cell lymphoma, extranodal natural killer cell (NK) T-cell lymphoma-nasal type, hepatosplenic T-cell lymphoma, or subcutaneous panniculitis-like T-cell lymphoma. In specific embodiments, the lymphoma is an EBV associated lymphoma. In specific embodiments, the lymphoma is AITL. In specific embodiments, the lymphoma is PTCL-NOS. In specific embodiments, the lymphoma is CTCL.

In some embodiments, the methods provided herein include determining the ratio of CXCL12 expression to CXCR4 expression in the sample from the subject having PTCL to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20.

In some embodiments, the methods provided herein include determining the ratio of CXCL12 expression to CXCR4 expression in the sample from the subject having leukemia to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20. In certain embodiments, the leukemia is AML. In specific embodiments, the AML is newly diagnosed. In specific embodiments, the subject is an elderly patient with poor-risk AML. In specific embodiments, the AML is relapsed or refractory AML. In specific embodiments, the leukemia is T-ALL. In specific embodiments, the leukemia is CIVIL.

In some embodiments, the methods provided herein include determining the ratio of CXCL12 expression to CXCR4 expression in the sample from the subject having MDS to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20.

In some embodiments, the methods provided herein include determining the ratio of CXCL12 expression to CXCR4 expression in the sample from the subject having myelofibrosis to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20.

In some embodiments, the methods provided herein include determining the ratio of CXCL12 expression to CXCR4 expression in the sample from the subject having Waldenström's macroglobulinemia to be higher than a reference ratio. In some embodiments, the reference ratio can be 1/10, 1/9, 1/8, 1/7, 1/6, 1/5, 1/4, 1/3, 1/2, 1, 2, 3, 4, 5, 6, 7, 8, 9, 10, or 20.

In some embodiments, the methods provided herein include determining the level of CXCL12 expression in a sample from a subject having cancer. In some embodiments, the methods provided herein include administering a therapeutically effective amount of an FTI to a subject having cancer if the level of a CXCL12 expression in a sample from the subject is higher than a reference level. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CML.

In some embodiments, the methods provided herein further include determining the level of CXCR4 expression in the sample from a subject having cancer. In some embodiments, the methods provided herein include administering a therapeutically effective amount of an FTI to a subject having cancer if the level of CXCR4 expression in a sample from the subject is lower than a reference level.

In some embodiments, the methods provided herein further include determining the ratio of the level of a CXCL12 expression to CXCR4 expression in the sample from a subject having cancer. In some embodiments, the methods provided herein include administering a therapeutically effective amount of an FTI to a subject having cancer if the ratio of the level of a CXCL12 expression to CXCR4 expression in a sample from the subject is higher than a reference ratio.

In some embodiments, the methods provided herein include determining the level of CXCL12 expression in a sample from a subject having lymphoma. In some embodiments, the methods provided herein include administering a therapeutically effective amount of an FTI to a subject having lymphoma if the level of a CXCL12 expression in a sample from the subject is higher than a reference level. In some embodiments, the lymphoma is AITL, PTCL-NOS, ALCL-ALK positive, ALCL-ALK negative, enteropathy-associated T-cell lymphoma, extranodal natural killer cell (NK) T-cell lymphoma-nasal type, hepatosplenic T-cell lymphoma, or subcutaneous panniculitis-like T-cell lymphoma. In specific embodiments, the lymphoma is an EBV associated lymphoma. In specific embodiments, the lymphoma is AITL. In specific embodiments, the lymphoma is PTCL-NOS. In specific embodiments, the lymphoma is CTCL.

In some embodiments, the methods provided herein further include determining the level of CXCR4 expression in the sample from a subject having lymphoma. In some embodiments, the methods provided herein include administering a therapeutically effective amount of an FTI to a subject having lymphoma if the level of CXCR4 expression in a sample from the subject is lower than a reference level.

In some embodiments, the methods provided herein further include determining the ratio of the level of a CXCL12 expression to CXCR4 expression in the sample from a subject having lymphoma. In some embodiments, the methods provided herein include administering a therapeutically effective amount of an FTI to a subject having lymphoma if the ratio of the level of a CXCL12 expression to CXCR4 expression in a sample from the subject is higher than a reference ratio.

In some embodiments, the methods provided herein include determining the level of CXCL12 expression in a sample from a subject having PTCL. In some embodiments, the methods provided herein include administering a therapeutically effective amount of an FTI to a subject having PTCL if the level of a CXCL12 expression in a sample from the subject is higher than a reference level.

In some embodiments, the methods provided herein further include determining the level of CXCR4 expression in the sample from a subject having PTCL. In some embodiments, the methods provided herein include administering a therapeutically effective amount of an FTI to a subject having PTCL if the level of CXCR4 expression in a sample from the subject is lower than a reference level.

In some embodiments, the methods provided herein further include determining the ratio of the level of a CXCL12 expression to CXCR4 expression in the sample from a subject having PTCL. In some embodiments, the methods provided herein include administering a therapeutically effective amount of an FTI to a subject having PTCL if the ratio of the level of a CXCL12 expression to CXCR4 expression in a sample from the subject is higher than a reference ratio.

In some embodiments, the methods provided herein include determining the level of CXCL12 expression in a sample from a subject having leukemia. In some embodiments, the methods provided herein include administering a therapeutically effective amount of an FTI to a subject having leukemia if the level of a CXCL12 expression in a sample from the subject is higher than a reference level. In certain embodiments, the leukemia is AML. In specific embodiments, the AML is newly diagnosed. In specific embodiments, the subject is an elderly patient with poor-risk AML. In specific embodiments, the AML is relapsed or refractory AML. In specific embodiments, the leukemia is T-ALL. In specific embodiments, the leukemia is CML.

In some embodiments, the methods provided herein further include determining the level of CXCR4 expression in the sample from a subject having leukemia. In some embodiments, the methods provided herein include administering a therapeutically effective amount of an FTI to a subject having leukemia if the level of CXCR4 expression in a sample from the subject is lower than a reference level.

In some embodiments, the methods provided herein further include determining the ratio of the level of a CXCL12 expression to CXCR4 expression in the sample from a subject having leukemia. In some embodiments, the methods provided herein include administering a therapeutically effective amount of an FTI to a subject having leukemia if the ratio of the level of a CXCL12 expression to CXCR4 expression in a sample from the subject is higher than a reference ratio.

In some embodiments, the methods provided herein include determining the level of CXCL12 expression in a sample from a subject having MDS. In some embodiments, the methods provided herein include administering a therapeutically effective amount of an FTI to a subject having MDS if the level of a CXCL12 expression in a sample from the subject is higher than a reference level.

In some embodiments, the methods provided herein further include determining the level of CXCR4 expression in the sample from a subject having MDS. In some embodiments, the methods provided herein include administering a therapeutically effective amount of an FTI to a subject having MDS if the level of CXCR4 expression in a sample from the subject is lower than a reference level.

In some embodiments, the methods provided herein further include determining the ratio of the level of a CXCL12 expression to CXCR4 expression in the sample from a subject having MDS. In some embodiments, the methods provided herein include administering a therapeutically effective amount of an FTI to a subject having MDS if the ratio of the level of a CXCL12 expression to CXCR4 expression in a sample from the subject is higher than a reference ratio.

In some embodiments, the methods provided herein include determining the level of CXCL12 expression in a sample from a subject having myelofibrosis. In some embodiments, the methods provided herein include administering a therapeutically effective amount of an FTI to a subject having myelofibrosis if the level of a CXCL12 expression in a sample from the subject is higher than a reference level.

In some embodiments, the methods provided herein further include determining the level of CXCR4 expression in the sample from a subject having myelofibrosis. In some embodiments, the methods provided herein include administering a therapeutically effective amount of an FTI to a subject having myelofibrosis if the level of CXCR4 expression in a sample from the subject is lower than a reference level.

In some embodiments, the methods provided herein further include determining the ratio of the level of a CXCL12 expression to CXCR4 expression in the sample from a subject having myelofibrosis. In some embodiments, the methods provided herein include administering a therapeutically effective amount of an FTI to a subject having myelofibrosis if the ratio of the level of a CXCL12 expression to CXCR4 expression in a sample from the subject is higher than a reference ratio.

In some embodiments, the methods provided herein include determining the level of CXCL12 expression in a sample from a subject having Waldenström's macroglobulinemia. In some embodiments, the methods provided herein include administering a therapeutically effective amount of an FTI to a subject having MDS if the level of a CXCL12 expression in a sample from the subject is higher than a reference level.

In some embodiments, the methods provided herein further include determining the level of CXCR4 expression in the sample from a subject having Waldenström's macroglobulinemia. In some embodiments, the methods provided herein include administering a therapeutically effective amount of an FTI to a subject having Waldenström's macroglobulinemia if the level of CXCR4 expression in a sample from the subject is lower than a reference level.

In some embodiments, the methods provided herein further include determining the ratio of the level of a CXCL12 expression to CXCR4 expression in the sample from a subject having Waldenström's macroglobulinemia. In some embodiments, the methods provided herein include administering a therapeutically effective amount of an FTI to a subject having Waldenström's macroglobulinemia if the ratio of the level of a CXCL12 expression to CXCR4 expression in a sample from the subject is higher than a reference ratio.

The expression level of a gene can refer to the protein level of the gene, or the RNA level of the gene. In some embodiments, the expression level of a gene refers to the protein level of the gene, and methods provided herein include determining the protein level of the gene.

In some embodiments, the methods provided herein include determining the expression level of KIR3DL2 mRNA in a sample from a subject having PTCL, and administering a therapeutically effective amount of an FTI to the subject if the KIR3DL2 mRNA expression level in the sample is lower than a reference level of KIR3DL2 mRNA.

In some embodiments, the methods provided herein include determining the mRNA level of a gene in a sample from a subject having cancer. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In specific embodiments, the cancer is leukemia. In specific embodiments, the leukemia is AML. In specific embodiments, the leukemia is T-ALL. In specific embodiments, the leukemia is CML. In some embodiments, the methods provided herein include determining the mRNA level of a gene in a sample from a subject having lymphoma. In specific embodiments, the lymphoma is an EBV associated lymphoma. In specific embodiments, the lymphoma is AITL. In specific embodiments, the lymphoma is CTCL. In some embodiments, the methods provided herein include determining the mRNA level of a gene in a sample from a subject having PTCL. In some embodiments, the methods provided herein include determining the mRNA level of a gene in a sample from a subject having MDS. In some embodiments, the methods provided herein include determining the mRNA level of a gene in a sample from a subject having myelofibrosis. In some embodiments, the methods provided herein include determining the mRNA level of a gene in a sample from a subject having Waldenström's macroglobulinemia. In some embodiments, the mRNA level of the gene is determined by Polymerase Chain Reaction (PCR), qPCR, qRT-PCR, RNA-seq, microarray analysis, SAGE, MassARRAY technique, next-generation sequencing, or FISH.

In some embodiments, the expression level of a gene refers to the mRNA level of the gene, and methods provided herein include determining the mRNA level of a gene. Methods to determine the mRNA level of a gene in a sample are well known in the art. For example, in some embodiments, the mRNA level can be determined by Polymerase Chain Reaction (PCR), qPCR, qRT-PCR, RNA-seq, microarray analysis, SAGE, MassARRAY technique, next-generation sequencing, or FISH.

Exemplary methods of detecting or quantitating mRNA levels include but are not limited to PCR-based methods, northern blots, ribonuclease protection assays, and the like. The mRNA sequence can be used to prepare a probe that is at least partially complementary. The probe can then be used to detect the mRNA sequence in a sample, using any suitable assay, such as PCR-based methods, Northern blotting, a dipstick assay, and the like.

The commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and polymerase chain reaction (PCR) (Weis et ah, Trends in Genetics 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

A sensitive and flexible quantitative method is PCR. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

It is noted, however, that other nucleic acid amplification protocols (i.e., other than PCR) may also be used in the nucleic acid analytical methods described herein. For example, suitable amplification methods include ligase chain reaction (see, e.g., Wu & Wallace, Genomics 4:560-569, 1988); strand displacement assay (see, e.g., Walker et al., Proc. Natl. Acad. Sci. USA 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., Proc. Natl. Acad. Sci. USA 86: 1173-1177, 1989); and self-sustained sequence replication (3SR) (Guatelli et al., Proc. Natl. Acad. Sci. USA 87: 1874-1878, 1990; WO 92/08800). Alternatively, methods that amplify the probe to detectable levels can be used, such as Q-replicase amplification (Kramer & Lizardi, Nature 339:401-402, 1989; Lomeli et al., Clin. Chem. 35: 1826-1831, 1989). A review of known amplification methods is provided, for example, by Abramson and Myers in Current Opinion in Biotechnology 4:41-47 (1993).

mRNA can be isolated from the sample. The sample can be a tissue sample. The tissue sample can be a tumour biopsy, such as a lymph node biopsy. General methods for mRNA extraction are well known in the art and are disclosed in standard textbooks of molecular biology, including Ausubel et al., Current Protocols of Molecular Biology, John Wiley and Sons (1997). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE® Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

In some embodiments, the first step in gene expression profiling by PCR is the reverse transcription of the RNA template into cDNA, followed by its exponential amplification in a PCR reaction. In other embodiments, a combined reverse-transcription-polymerase chain reaction (RT-PCR) reaction may be used, e.g., as described in U.S. Pat. Nos. 5,310,652; 5,322,770; 5,561,058; 5,641,864; and 5,693,517. The two commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP™ RNA PCR kit (Perkin Elmer, Calif., USA), following the manufacturer's instructions. The derived cDNA can then be used as a template in the subsequent PCR reaction.

In some embodiments, Real-Time Reverse Transcription-PCR (qRT-PCR) can be used for both the detection and quantification of RNA targets (Bustin, et al., 2005, *Clin. Sci.*, 109:365-379). Examples of qRT-PCR-based methods can be found, for example, in U.S. Pat. No. 7,101,663, which is incorporated by reference herein in its entirety. Instruments for real-time PCR, such as the Applied Biosystems 7500, are available commercially, as are the reagents, such as TaqMan Sequence Detection chemistry.

For example, TaqMan Gene Expression Assays can be used, following the manufacturer's instructions. These kits are pre-formulated gene expression assays for rapid, reliable detection and quantification of human, mouse and rat mRNA transcripts. TaqMan® or 5'-nuclease assay, as described in U.S. Pat. Nos. 5,210,015; 5,487,972; and 5,804,375; and Holland et al., 1988, Proc. Natl. Acad. Sci. USA 88:7276-7280, can be used. TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes.

Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification. 5'-Nuclease assay data may be initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

PCR primers and probes are designed based upon intron sequences present in the gene to be amplified. In this embodiment, the first step in the primer/probe design is the delineation of intron sequences within the genes. This can be done by publicly available software, such as the DNA BLAST software developed by Kent, W., Genome Res. 12(4):656-64 (2002), or by the BLAST software including its variations. Subsequent steps follow well established methods of PCR primer and probe design.

In order to avoid non-specific signals, it can be important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Rozen and Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386).

RNA-Seq, also called Whole Transcriptome Shotgun Sequencing (WTSS) refers to the use of high-throughput sequencing technologies to sequence cDNA in order to get information about a sample's RNA content. Publications describing RNA-Seq include: Wang et al., Nature Reviews Genetics 10 (1): 57-63 (January 2009); Ryan et al. BioTechniques 45 (1): 81-94 (2008); and Maher et al., Nature 458 (7234): 97-101 (January 2009); which are hereby incorporated in their entirety.

Differential gene expression can also be identified, or confirmed using the microarray technique. In this method, polynucleotide sequences of interest (including cDNAs and oligonucleotides) are plated, or arrayed, on a microchip substrate. The arrayed sequences are then hybridized with specific DNA probes from cells or tissues of interest.

In an embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2): 106-149 (1996)). Microarray analysis can be performed by commercially available equipment, following manufacturer's protocols, such as by using the Affymetrix GENCHIP™ technology, or Incyte's microarray technology.

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et ah, Science 270:484-487 (1995); and Velculescu et al, Cell 88:243-51 (1997).

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dispensed on a chip array that is pre-loaded with the components needed for MALTI-TOF MS sample preparation. The various cDNAs present in the reaction are quantitated by analyzing the peak areas in the mass spectrum obtained.

mRNA level can also be measured by an assay based on hybridization. A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Any suitable assay platform can be used to determine the mRNA level in a sample. For example, an assay can be in the form of a dipstick, a membrane, a chip, a disk, a test strip, a filter, a microsphere, a slide, a multiwell plate, or an optical fiber. An assay system can have a solid support on which a nucleic acid corresponding to the mRNA is attached. The solid support can have, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4', 5' dichloro 2', 7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethyl-aminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions can be employed.

Hybridization is typically performed under stringent hybridization conditions. Standard hybridization techniques (e.g. under conditions sufficient to provide for specific binding of target mRNAs in the sample to the probes) are described in Kallioniemi et al., Science 258:818-821 (1992) and WO 93/18186. Several guides to general techniques are available, e.g., Tijssen, *Hybridization with Nucleic Acid Probes, Parts I and II* (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art. Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Any methods as described herein or otherwise known in the art can be used to determine the mRNA level of a gene in a sample from a subject described herein. By way of example, in some embodiments, provided herein are methods to treat PTCL in a subject that include determining the mRNA level of the CXCL12 gene in a sample from the subject by using qRT-PCR, and administering a therapeutically effective amount of an FTI to the subject if the mRNA level of the CXCL12 gene in the sample is higher than a reference expression level of the CXCL12 gene.

In some embodiments, the methods provided herein to treat CXCL12-expressing lymphoma in a subject with an FTI, methods to predict the responsiveness of a subject having lymphoma for an FTI treatment, methods to select a lymphoma patient for an FTI treatment, methods to stratify lymphoma patients for an FTI treatment, and methods to increase the responsiveness of a lymphoma patient population for an FTI treatment further include determining the expression level of an AITL marker selected from the group consisting of CXCL13 and PD-1, in a sample from a subject having lymphoma, wherein if the expression level of the additional gene in the sample is higher than a reference expression level, the subject is predicted to be likely responsive to an FTI treatment, or is administered an therapeutically effective amount of an FTI.

In some embodiments, the methods provided herein further include determining the SNV status of CXCL12 in a sample from a subject having leukemia (e.g., AML, T-ALL, or CML). In some embodiments, a subject having leukemia (e.g., AML, T-ALL, or CML) is predicted to be likely responsive to an FTI treatment, or is administered a therapeutically effective amount of an FTI if the sample does not have the rs2839695 SNV of CXCL12 (A/G at position 44873849 in the CXCL12 3' untranslated region (UTR)). In some embodiments, a subject having leukemia (e.g., AML, T-ALL, or CIVIL) is predicted to be likely responsive to an FTI treatment, or is administered a therapeutically effective amount of an FTI if the sample does not have an SNV at position 44873186 of the 3' UTR of CXCL12. In some embodiments, a subject having leukemia (e.g., AML, T-ALL, or CIVIL) is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of CXCL12 in a sample from a subject having lymphoma (e.g., CTCL). In some embodiments, a subject having lymphoma (e.g., CTCL) is predicted to be likely responsive to an FTI treatment, or is administered a therapeutically effective amount of an FTI if the sample does not have the rs2839695 SNV of CXCL12 (A/G at position 44873849 in the CXCL12 3' untranslated region (UTR)). In some embodiments, a subject having lymphoma (e.g., CTCL) is predicted to be likely responsive to an FTI treatment, or is administered a therapeutically effective amount of an FTI if the sample does not have an SNV at position 44873186 of the 3' UTR of CXCL12. In some embodiments, a subject having lymphoma (e.g., CTCL) is predicted to be likely responsive to an FTI treatment, or is administered a therapeutically effective amount of an FTI if the sample does not have an SNV in the 3' UTR of CXCL12. In specific embodiments, the lymphoma is an EBV associated lymphoma. In specific embodiments, the lymphoma is CTCL.

In some embodiments, the methods provided herein further include determining the SNV status of CXCL12 in a sample from a subject having PTCL. In some embodiments, a subject having PTCL is predicted to be likely responsive to an FTI treatment, or is administered a therapeutically effective amount of an FTI if the sample does not have the rs2839695 SNV of CXCL12 (A/G at position 44873849 in the CXCL12 3' untranslated region (UTR)). In some embodiments, a subject having PTCL is predicted to be likely responsive to an FTI treatment, or is administered a therapeutically effective amount of an FTI if the sample does not have an SNV at position 44873186 of the 3' UTR of CXCL12. In some embodiments, a subject having PTCL is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of CXCL12 in a sample from a subject having MDS. In some embodiments, a subject having MDS is predicted to be likely responsive to an FTI treatment, or is administered a therapeutically effective amount of an FTI if the sample does not have the rs2839695 SNV of CXCL12 (A/G at position 44873849 in the CXCL12 3' untranslated region (UTR)). In some embodiments, a subject having MDS is predicted to be likely responsive to an FTI treatment, or is administered a therapeutically effective amount of an FTI if the sample does not have an SNV at position 44873186 of the 3' UTR of CXCL12. In some embodiments, a subject having MDS is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of CXCL12 in a sample from a subject having myelofibrosis. In some embodiments, a subject having myelofibrosis is predicted to be likely responsive to an FTI treatment, or is administered a therapeutically effective amount of an FTI if the sample does not have the rs2839695 SNV of CXCL12 (A/G at position 44873849 in the CXCL12 3' untranslated region (UTR)). In some embodiments, a subject having myelofibrosis is predicted to be likely responsive to an FTI treatment, or is administered a therapeutically effective amount of an FTI if the sample does not have an SNV at position 44873186 of the 3' UTR of CXCL12. In some embodiments, a subject having myelofibrosis is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of CXCL12 in a sample from a subject having Waldenström's macroglobulinemia. In some embodiments, a subject having Waldenström's macroglobulinemia is predicted to be likely responsive to an FTI treatment, or is administered a therapeutically effective amount of an FTI if the sample does not have the rs2839695 SNV of CXCL12 (A/G at position 44873849 in the CXCL12 3' untranslated region (UTR)). In some embodiments, a subject having Waldenström's macroglobulinemia is predicted to be likely responsive to an FTI treatment, or is administered a therapeutically effective amount of an FTI if the sample does not have an SNV at position 44873186 of the 3' UTR of CXCL12. In some embodiments, a subject having Waldenström's macroglobulinemia is predicted to be likely responsive to an FTI treatment, or is administered a therapeutically effective amount of an FTI if the sample does not have an SNV in the 3' UTR of CXCL12.

In some embodiments, the methods provided herein further include determining the SNV status of SIK3 in a sample from a subject having cancer. In some embodiments, a subject having cancer is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having cancer is predicted to be likely responsive to an FTI treatment, or is administered a therapeutically effective amount of an FTI if the sample has a SIK3 SNV. In specific embodiments, the SIK3 SNV is N559H. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CIVIL.

In some embodiments, the methods provided herein further include determining the SNV status of SIK3 in a sample from a subject having lymphoma. In some embodiments, a subject having lymphoma is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having lymphoma is predicted to be likely responsive to an FTI treatment, or is administered a therapeutically effective amount of an FTI if the sample has a SIK3 SNV. In specific embodiments, the SIK3 SNV is N559H. In specific embodiments, the lymphoma is an EBV associated lymphoma. In specific embodiments, the lymphoma is CTCL.

In some embodiments, the methods provided herein further include determining the SNV status of SIK3 in a sample from a subject having PTCL. In some embodiments, a subject having PTCL is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is 51163G. In some embodiments, a subject having PTCL is predicted to be likely responsive to an FTI treatment, or is administered a therapeutically effective amount of an FTI if the sample has a SIK3 SNV. In specific embodiments, the SIK3 SNV is N559H.

In some embodiments, the methods provided herein further include determining the SNV status of SIK3 in a sample from a subject having MDS. In some embodiments, a subject having MDS is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having MDS is predicted to be likely responsive to an FTI treatment, or is administered a therapeutically effective amount of an FTI if the sample has a SIK3 SNV. In specific embodiments, the SIK3 SNV is N559H.

In some embodiments, the methods provided herein further include determining the SNV status of SIK3 in a sample from a subject having myelofibrosis. In some embodiments, a subject having myelofibrosis is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is 51163G. In some embodiments, a subject having myelofibrosis is predicted to be likely responsive to an FTI treatment, or is administered a therapeutically effective amount of an FTI if the sample has a SIK3 SNV. In specific embodiments, the SIK3 SNV is N559H.

In some embodiments, the methods provided herein further include determining the SNV status of SIK3 in a sample from a subject having Waldenström's macroglobulinemia. In some embodiments, a subject having Waldenström's macroglobulinemia is predicted to be likely responsive to an FTI treatment, or is administered a therapeutically effective amount of an FTI if the sample has an SNV in the N-terminal coding sequence of SIK3. In specific embodiments, the SNV in the N-terminal coding sequence is S986Y. In specific embodiments, the SNV in the N-terminal coding sequence is P1076R. In specific embodiments, the SNV in the N-terminal coding sequence is P1136R. In specific embodiments, the SNV in the N-terminal coding sequence is S1163G. In some embodiments, a subject having Waldenström's macroglobulinemia is predicted to be likely responsive to an FTI treatment, or is administered a therapeutically effective amount of an FTI if the sample has a SIK3 SNV. In specific embodiments, the SIK3 SNV is N559H.

In some embodiments, the methods provided herein further include determining the SNV status of CENPF in a sample from a subject having cancer. In some embodiments, a subject having cancer is predicted to be likely responsive to an FTI treatment, or is administered a therapeutically effective amount of an FTI if the sample has the R2729Q gene variant. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CML.

In some embodiments, the methods provided herein further include determining the SNV status of CENPF in a sample from a subject having lymphoma. In some embodiments, a subject having lymphoma is predicted to be likely responsive to an FTI treatment, or is administered a therapeutically effective amount of an FTI if the sample has the R2729Q gene variant. In specific embodiments, the lymphoma is an EBV associated lymphoma. In specific embodiments, the lymphoma is CTCL.

In some embodiments, the methods provided herein further include determining the SNV status of CENPF in a sample from a subject having PTCL. In some embodiments, a subject having PTCL is predicted to be likely responsive to an FTI treatment, or is administered a therapeutically effective amount of an FTI if the sample has the R2729Q gene variant.

In some embodiments, the methods provided herein further include determining the SNV status of CENPF in a sample from a subject having MDS. In some embodiments, a subject having MDS is predicted to be likely responsive to an FTI treatment, or is administered a therapeutically effective amount of an FTI if the sample has the R2729Q gene variant.

In some embodiments, the methods provided herein further include determining the SNV status of CENPF in a sample from a subject having myelofibrosis. In some embodiments, a subject having myelofibrosis is predicted to be likely responsive to an FTI treatment, or is administered a therapeutically effective amount of an FTI if the sample has the R2729Q gene variant.

In some embodiments, the methods provided herein further include determining the SNV status of CENPF in a sample from a subject having Waldenström's macroglobulinemia. In some embodiments, a subject having Waldenström's macroglobulinemia is predicted to be likely responsive to an FTI treatment, or is administered a therapeutically effective amount of an FTI if the sample has the R2729Q gene variant.

Methods for determining SNV and/or mutation status by analyzing nucleic acids are well known in the art. In some embodiments, the methods include sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In some embodiments, the SNV and/or mutation status is determined using standard sequencing methods, including, for example, Sanger sequencing, next generation sequencing (NGS). In some embodiments, the SNV and/or mutation status is determined using MS.

In some embodiments, the methods provided herein include determining the expression level of CXCL12 protein in a sample from a subject having cancer, and administering a therapeutically effective amount of an FTI to the subject if the CXCL12 protein expression level in the sample is higher than a reference level of CXCL12 protein. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In some embodiments, the cancer is a hematologic cancer. In certain embodiments, the cancer is a lymphoma. In specific embodiments, the lymphoma is CTCL. In certain embodiments, the cancer is leukemia. In specific embodiments, the leukemia is AML. In specific embodiments, the leukemia is T-ALL. In specific embodiments, the leukemia is CML.

In some embodiments, the methods provided herein include determining the expression level of CXCL12 protein in a sample from a subject having lymphoma, and administering a therapeutically effective amount of an FTI to the subject if the CXCL12 protein expression level in the sample is higher than a reference level of CXCL12 protein. In specific embodiments, the lymphoma is an EBV associated lymphoma. In specific embodiments, the lymphoma is AITL. In specific embodiments, the lymphoma is PTCL-NOS. In specific embodiments, the lymphoma is CTCL.

In some embodiments, the methods provided herein include determining the expression level of CXCL12 protein in a sample from a subject having PTCL, and administering a therapeutically effective amount of an FTI to the subject if the CXCL12 protein expression level in the sample is higher than a reference level of CXCL12 protein.

In some embodiments, the methods provided herein include determining the expression level of CXCL12 protein in a sample from a subject having MDS, and administering a therapeutically effective amount of an FTI to the subject if the CXCL12 protein expression level in the sample is higher than a reference level of CXCL12 protein.

In some embodiments, the methods provided herein include determining the expression level of CXCL12 protein in a sample from a subject having myelofibrosis, and administering a therapeutically effective amount of an FTI to the subject if the CXCL12 protein expression level in the sample is higher than a reference level of CXCL12 protein.

In some embodiments, the methods provided herein include determining the expression level of CXCL12 protein in a sample from a subject having Waldenström's macroglobulemia, and administering a therapeutically effective amount of an FTI to the subject if the CXCL12 protein expression level in the sample is higher than a reference level of CXCL12 protein.

In some embodiments, the methods provided herein include determining the expression level of KIR3DL2 protein in a sample from a subject having PTCL, and administering a therapeutically effective amount of an FTI to the subject if the KIR3DL2 protein expression level in the sample is lower than a reference level of KIR3DL2 protein. In certain embodiments, the KIR3DL2 protein expression is determined by IHC. In certain embodiments, the KIR3DL2 protein expression is determined by FACS.

In some embodiments, the methods provided herein include determining the protein level of a gene in a sample from a subject having cancer. In specific embodiments, the cancer is nasopharyngeal carcinoma. In specific embodiments, the cancer is an EBV associated nasopharyngeal carcinoma. In specific embodiments, the cancer is esophageal cancer. In specific embodiments, the cancer is ovarian cancer. In specific embodiments, the cancer is breast cancer. In certain embodiments, the cancer is pancreatic cancer. In specific embodiments, the pancreatic cancer is locally advanced pancreatic cancer. In specific embodiments, the cancer is leukemia. In specific embodiments, the leukemia is T-ALL. In specific embodiments, the leukemia is CIVIL. In some embodiments, the methods provided herein include determining the protein level of a gene in a sample from a subject having lymphoma. In specific embodiments, the lymphoma is an EBV associated lymphoma. In specific embodiments, the lymphoma is AITL. In specific embodiments, the lymphoma is CTCL. In some embodiments, the methods provided herein include determining the protein level of a gene in a sample from a subject having PTCL. In some embodiments, the methods provided herein include determining the protein level of a gene in a sample from a subject having MDS. In some embodiments, the methods provided herein include determining the protein level of a gene in a sample from a subject having myelofibrosis. In some embodiments, the methods provided herein include determining the protein level of a gene in a sample from a subject having Waldenström's macroglobulemia. In some embodiments, the protein level of the gene can be determined by an immunohistochemistry (IHC) assay, an immunoblotting (TB) assay, an immunofluorescence (IF) assay, flow cytometry (FACS), or an Enzyme-Linked Immunosorbent Assay (ELISA). The IHC assay can be H&E staining.

Methods to determine a protein level of a gene in a sample are well known in the art. For example, in some embodiments, the protein level can be determined by an immunohistochemistry (IHC) assay, an immunoblotting (IB) assay, an immunofluorescence (IF) assay, flow cytometry (FACS), or an Enzyme-Linked Immunosorbent Assay (ELISA). In some embodiments, the protein level can be determined by Hematoxylin and Eosin stain ("H&E staining").

The protein level of the gene can be detected by a variety of (IHC) approaches or other immunoassay methods. IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, including for example, polyclonal antisera, or monoclonal antibodies specific for each gene are used to detect expression. As discussed in greater detail below, the antibodies can be detected by direct labelling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Ten, eds., 7th ed. 1991).

Commonly used assays to detect protein level of a gene include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum, a tumor biopsy, a lymph node, or bone marrow.

A wide range of immunoassay techniques using such an assay format are available, see, e.g., U.S. Pat. Nos. 4,016, 043, 4,424,279, and 4,018,653, which are hereby incorporated by reference in their entireties. These include both single-site and two-site or "sandwich" assays of the non-competitive types, as well as in the traditional competitive binding assays. These assays also include direct binding of a labeled antibody to a target gene. Sandwich assays are commonly used assays. A number of variations of the sandwich assay technique exist. For example, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of the gene.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the gene is either covalently or passively bound to a solid surface. The solid surface may be glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the gene. The second antibody is linked to a reporter molecule which is used to indicate the binding of the second antibody to the molecular marker.

In some embodiments, flow cytometry (FACS) can be used to detect the protein level of a gene that is expressed on the surface of the cells. Genes that are surface proteins (such as CXCR3) can be detected using antibodies against these genes. The flow cytometer detects and reports the intensity of the fluorichrome-tagged antibody, which indicates the expression level of the gene. Non-fluorescent cytoplasmic proteins can also be observed by staining permeablized cells. The stain can either be a fluorescence compound able to bind to certain molecules, or a fluorichrome-tagged antibody to bind the molecule of choice.

An alternative method involves immobilizing the target gene in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by a labeled reporter molecule.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of gene which was present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art and are discussed herein.

Any methods as described herein or otherwise known in the art can be used to determine the protein level of a gene in a sample from a subject described herein. By way of example, in some embodiments, provided herein are methods to treat PTCL in a subject that include determining the protein level of a CXCL12 gene in a sample from the subject by using an IF assay, and administering a therapeutically effective amount of an FTI to the subject if the protein level of the CXCL12 gene in the sample is higher than a reference expression level of the CXCL12 gene.

In some embodiments, the methods provided herein include determining the proportion of cells expressing KIR3DL2 in a sample from a subject having PTCL, and administering a therapeutically effective amount of an FTI to the subject if the proportion of cells expressing KIR3DL2 in the sample is lower than a reference level.

Methods to analyze the cell constitution of a sample from a subject are well known in the art, including such as an immunohistochemistry (IHC) assay, an immunofluorescence (IF) assay, and flow cytometry (FACS).

In some embodiments, the cell constitution is determined by an IHC assay. A variety of IHC assays are described herein. By way of example, in some embodiments, an IHC staining can be performed on deparaffinised tissue section with antibody that binds to the protein of interest, incubating overnight at 4° C., after peroxidise and protein blocking. The microwave epitope retrieval in 10 mM Tris/HCl PH9 containing 1 mM ethylenediamine tetraacetic acid can be used for the antibody and appropriate negative control (no primary antibody) and positive controls (tonsil or breast tumor sections) can be stained in parallel with each set of tumor studied. See e.g., Iqbal et al., *Blood* 123(19): 2915-23 (2014).

In some embodiments, the cell constitution is determined by flow cytometry (FACS). Various methods of using FACS to identify and enumerate specific T cell subsets are well known in the art and commercially available. Cell surface markers can be used to identify a specific cell population. By evaluating the unique repertoire of cell surface markers using several antibodies together, each coupled with a different fluorochromes, a given cell population can be identified and quantified. The available technologies include the multicolour flow cytometry technology by BD Biosciences, flow cytometry immunophenotyping technology by Abcam, etc. Various gating and data analysis strategies can be used to distinguish cell populations.

In some embodiments, provided herein are methods that include analyzing the cell constitution of a blood sample from a subject using flow cytometry.

Any methods for analyzing expression levels (e.g., the protein level or the mRNA level) as described herein or otherwise known in the art can be used to determine the level of the additional gene in a sample, such as an IHC assay, an D3 assay, an IF assay, FACS, ELISA, protein microarray analysis, qPCR, qRT-PCR, RNA-seq, RNA microarray analysis, SAGE, MassARRAY technique, next-generation sequencing, or FISH.

B. Pharmaceutical Compositions

In some embodiments, provided herein is a method of treating a subject with an FTI or a pharmaceutical composition having FTI. The pharmaceutical compositions provided herein contain therapeutically effective amounts of an FTI and a pharmaceutically acceptable carrier, diluent or excipient. In some embodiments, the FTI is tipifarnib; arglabin; perrilyl alcohol; SCH-66336; L778123; L739749; FTI-277; L744832; R208176; BMS 214662; AZD3409; or CP-609,754. In some embodiments, the FTI is tipifarnib.

The FTI can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the FTI is formulated into pharmaceutical compositions using techniques and procedures well known in the art (see, e.g., Ansel Introduction to Pharmaceutical Dosage Forms, Seventh Edition 1999).

In the compositions, effective concentrations of the FTI and pharmaceutically acceptable salts is (are) mixed with a suitable pharmaceutical carrier or vehicle. In certain embodiments, the concentrations of the FTI in the compositions are effective for delivery of an amount, upon administration, that treats, prevents, or ameliorates one or more of the symptoms and/or progression of cancer, including haematological cancers and solid tumors.

The compositions can be formulated for single dosage administration. To formulate a composition, the weight fraction of the FTI is dissolved, suspended, dispersed or otherwise mixed in a selected vehicle at an effective concentration such that the treated condition is relieved or ameliorated. Pharmaceutical carriers or vehicles suitable for administration of the FTI provided herein include any such carriers known to those skilled in the art to be suitable for the particular mode of administration.

In addition, the FTI can be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of an FTI provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The FTI is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of FTI in the pharmaceutical composition will depend on absorption, tissue distribution, inactivation and excretion rates of the FTI, the physicochemical characteristics of the FTI, the dosage schedule, and amount administered as well as other factors known to those of skill in the art. For example, the amount that is delivered is sufficient to ameliorate one or more of the symptoms of cancer, including hematopoietic cancers and solid tumors.

In certain embodiments, a therapeutically effective dosage should produce a serum concentration of active ingredient of from about 0.1 ng/ml to about 50-100 µg/ml. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The FTI may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfate; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the FTI exhibits insufficient solubility, methods for solubilizing compounds can be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1-85% or about 75-95%.

The FTI or pharmaceutically acceptable salts can be prepared with carriers that protect the compound against rapid elimination from the body, such as time release formulations or coatings.

The compositions can include other active compounds to obtain desired combinations of properties. The compounds provided herein, or pharmaceutically acceptable salts thereof as described herein, can also be administered together with another pharmacological agent known in the general art to be of value in treating one or more of the diseases or medical conditions referred to hereinabove, such as diseases related to oxidative stress.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Parenteral administration, generally characterized by injection, either subcutaneously, intramuscularly or intravenously is also provided herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the FTI is adjusted so that an injection provides an effective amount to produce the desired pharmacological effect. The exact dose depends on the age, weight and condition of the patient or animal as is known in the art. The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an FTI is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The FTI can be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Of interest herein are also lyophilized powders, which can be reconstituted for administration as solutions, emulsions and other mixtures. They can also be reconstituted and formulated as solids or gels.

The sterile, lyophilized powder is prepared by dissolving an FTI provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The FTI or pharmaceutical composition having an FTI can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The FTI or pharmaceutical composition having an FTI can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Other routes of administration, such as transdermal patches, and rectal administration are also contemplated herein. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams. Tablets and capsules for rectal administration are manufactured using the same pharmaceutically acceptable substance and by the same methods as for formulations for oral administration.

The FTI or pharmaceutical composition having an FTI provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of FTI using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the FTI can be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The F can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

The FTI or pharmaceutical composition of FTI can be packaged as articles of manufacture containing packaging material, a compound or pharmaceutically acceptable salt thereof provided herein, which is used for treatment, prevention or amelioration of one or more symptoms or progression of cancer, including haematological cancers and solid tumors, and a label that indicates that the compound or pharmaceutically acceptable salt thereof is used for treatment, prevention or amelioration of one or more symptoms or progression of cancer, including haematological cancers and solid tumors.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

In some embodiments, a therapeutically effective amount of the pharmaceutical composition having an FTI is administered orally or parenterally. In some embodiments, the pharmaceutical composition having tipifarnib as the active ingredient and is administered orally in an amount of from 1 up to 1500 mg/kg daily, either as a single dose or subdivided into more than one dose, or more particularly in an amount of from 10 to 1200 mg/kg daily. In some embodiments, the pharmaceutical composition having tipifarnib as the active ingredient and is administered orally in an amount of 100 mg/kg daily, 200 mg/kg daily, 300 mg/kg daily, 400 mg/kg daily, 500 mg/kg daily, 600 mg/kg daily, 700 mg/kg daily, 800 mg/kg daily, 900 mg/kg daily, 1000 mg/kg daily, 1100 mg/kg daily, or 1200 mg/kg daily. In some embodiments, the FTI is tipifarnib.

In some embodiments, the FTI is administered at a dose of 200-1500 mg daily. In some embodiments, the FTI is administered at a dose of 200-1200 mg daily. In some embodiments, the FTI is administered at a dose of 200 mg daily. In some embodiments, the FTI is administered at a dose of 300 mg daily. In some embodiments, the FTI is administered at a dose of 400 mg daily. In some embodiments, the FTI is administered at a dose of 500 mg daily. In some embodiments, the FTI is administered at a dose of 600 mg daily. In some embodiments, the FTI is administered at a dose of 700 mg daily. In some embodiments, the FTI is administered at a dose of 800 mg daily. In some embodiments, the FTI is administered at a dose of 900 mg daily. In some embodiments, the FTI is administered at a dose of 1000 mg daily. In some embodiments, the FTI is administered at a dose of 1100 mg daily. In some embodiments, the FTI is administered at a dose of 1200 mg daily. In some embodiments, an FTI is administered at a dose of 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, or 1200 mg daily. In some embodiments, the FTI is administered at a dose of 1300 mg daily. In some embodiments, the FTI is administered at a dose of 1400 mg daily. In some embodiments, the FTI is tipifarnib.

In some embodiments, the FTI is administered at a dose of 200-1400 mg b.i.d. In some embodiments, the FTI is administered at a dose of 300-1200 mg b.i.d. In some embodiments, the FTI is administered at a dose of 300-900 mg b.i.d. In some embodiments, the FTI is administered at a dose of 600 mg b.i.d. In some embodiments, the FTI is administered at a dose of 700 mg b.i.d. In some embodiments, the FTI is administered at a dose of 800 mg b.i.d. In some embodiments, the FTI is administered at a dose of 900 mg b.i.d. In some embodiments, the FTI is administered at a dose of 1000 mg b.i.d. In some embodiments, the FTI is administered at a dose of 1100 mg b.i.d. In some embodiments, the FTI is administered at a dose of 1200 mg b.i.d. In some embodiments, an FTI is administered at a dose of 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, or 1200 mg b.i.d. In some embodiments, the FTI for use in the compositions and methods provided herein is tipifarnib.

As a person of ordinary skill in the art would understand, the dosage varies depending on the dosage form employed, condition and sensitivity of the patient, the route of administration, and other factors. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. During a treatment cycle, the daily dose could be varied. In some embodiments, a starting dosage can be titrated down within a treatment cycle. In some embodiments, a starting dosage can be titrated up within a treatment cycle. The final dosage can depend on the occurrence of dose limiting toxicity and other factors. In some embodiments, the FTI is administered at a starting dose of 300 mg daily and escalated to a maximum dose of 400 mg, 500 mg, 600 mg, 700 mg, 800 mg, 900 mg, 1000 mg, 1100 mg, or 1200 mg daily. In some embodiments, the FTI is administered at a starting dose of 400 mg daily and escalated to a maximum dose of 500 mg, 600 mg, 700 mg, 800 mg, 900 mg, 1000 mg, 1100 mg, or 1200 mg daily. In some embodiments, the FTI is administered at a starting dose of 500 mg daily and escalated to a maximum dose of 600 mg, 700 mg, 800 mg, 900 mg, 1000 mg, 1100 mg, or 1200 mg daily. In some embodiments, the FTI is administered at a starting dose of 600 mg daily and escalated to a maximum dose of 700 mg, 800 mg, 900 mg, 1000 mg, 1100 mg, or 1200 mg daily. In some embodiments, the FTI is administered at a starting dose of 700 mg daily and escalated to a maximum dose of 800 mg, 900 mg, 1000 mg, 1100 mg, or 1200 mg daily. In some embodiments, the FTI is administered at a starting dose of 800 mg daily and escalated to a maximum dose of 900 mg, 1000 mg, 1100 mg, or 1200 mg daily. In some embodiments, the FTI is administered at a starting dose of 900 mg daily and escalated to a maximum dose of 1000 mg, 1100 mg, or 1200 mg daily. The dose escalation can be done at once, or step wise. For example, a starting dose at 600 mg daily can be escalated to a final dose of 1000 mg daily by increasing by 100 mg per day over the course of 4 days, or by increasing by 200 mg per day over the course of 2 days, or by increasing by 400 mg at once. In some embodiments, the FTI is tipifarnib.

In some embodiments, the FTI is administered at a relatively high starting dose and titrated down to a lower dose depending on the patient response and other factors. In some embodiments, the FTI is administered at a starting dose of 1200 mg daily and reduced to a final dose of 1100 mg, 1000 mg, 900 mg, 800 mg, 700 mg, 600 mg, 500 mg, 400 mg, or 300 mg daily. In some embodiments, the FTI is administered at a starting dose of 1100 mg daily and reduced to a final dose of 1000 mg, 900 mg, 800 mg, 700 mg, 600 mg, 500 mg, 400 mg, or 300 mg daily. In some embodiments, the FTI is administered at a starting dose of 1000 mg daily and reduced to a final dose of 900 mg, 800 mg, 700 mg, 600 mg, 500 mg, 400 mg, or 300 mg daily. In some embodiments, the FTI is administered at a starting dose of 900 mg daily and reduced to a final dose of 800 mg, 700 mg, 600 mg, 500 mg, 400 mg, or 300 mg daily. In some embodiments, the FTI is administered at a starting dose of 800 mg daily and reduced to a final dose of 700 mg, 600 mg, 500 mg, 400 mg, or 300 mg daily. In some embodiments, the FTI is administered at a starting dose of 600 mg daily and reduced to a final dose of 500 mg, 400 mg, or 300 mg daily. The dose reduction can be done at once, or step wise. In some embodiments, the FTI is tipifarnib. For example, a starting dose at 900 mg daily can be reduced to a final dose of 600 mg daily by decreasing by 100 mg per day over the course of 3 days, or by decreasing by 300 mg at once.

A treatment cycle can have different length. In some embodiments, a treatment cycle can be one week, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, or 12 months. In some embodiments, a treatment cycle is 4 weeks. A treatment cycle can have intermittent schedule. In some embodiments, a 2-week treatment cycle can have 5-day dosing followed by 9-day rest. In some embodiments, a 2-week treatment cycle can have 6-day dosing followed by 8-day rest. In some embodiments, a 2-week treatment cycle can have 7-day dosing followed by 7-day rest. In some embodiments, a 2-week treatment cycle can have 8-day dosing followed by 6-day rest. In some embodiments, a 2-week treatment cycle can have 9-day dosing followed by 5-day rest.

In some embodiments, the FTI is administered daily for 3 of out of 4 weeks in repeated 4 week cycles. In some embodiments, the FTI is administered daily in alternate weeks (one week on, one week off) in repeated 4 week cycles. In some embodiments, the FTI is administered at a dose of 300 mg b.i.d. orally for 3 of out of 4 weeks in repeated 4 week cycles. In some embodiments, the FTI is administered at a dose of 600 mg b.i.d. orally for 3 of out of 4 weeks in repeated 4 week cycles. In some embodiments, the FTI is administered at a dose of 900 mg b.i.d. orally in alternate weeks (one week on, one week off) in repeated 4 week cycles. In some embodiments, the FTI is administered at a dose of 1200 mg b.i.d. orally in alternate weeks (days 1-7 and 15-21 of repeated 28-day cycles). In some embodiments, the FTI is administered at a dose of 1200 mg b.i.d. orally for days 1-5 and 15-19 out of repeated 28-day cycles.

In some embodiments, a 900 mg bid tipifarnib alternate week regimen can be used adopted. Under the regimen, patients receive a starting dose of 900 mg, po, bid on days 1-7 and 15-21 of 28-day treatment cycles. In the absence of unmanageable toxicities, subjects can continue to receive the tipifarnib treatment for up to 12 months. The dose can also be increased to 1200 mg bid if the subject is tolerating the treatment well. Stepwise 300 mg dose reductions to control treatment-related, treatment-emergent toxicities can also be included.

In some other embodiments, tipifarnib is given orally at a dose of 300 mg bid daily for 21 days, followed by 1 week of rest, in 28-day treatment cycles (21-day schedule; Cheng D T, et al., *J Mol Diagn*. (2015) 17(3):251-64). In some embodiments, a 5-day dosing ranging from 25 to 1300 mg bid followed by 9-day rest is adopted (5-day schedule; Zujewski J., *J Clin Oncol.*, (2000) February; 18(4):927-41). In some embodiments, a 7-day bid dosing followed by 7-day rest is adopted (7-day schedule; Lara P N Jr., *Anticancer Drugs*., (2005) 16(3):317-21; Kirschbaum M H, *Leukemia*., (2011) October; 25(10):1543-7). In the 7-day schedule, the patients can receive a starting dose of 300 mg bid with 300 mg dose escalations to a maximum planned dose of 1800 mg bid. In the 7-day schedule study, patients can also receive tipifarnib bid on days 1-7 and days 15-21 of 28-day cycles at doses up to 1600 mg bid.

In previous studies FTI were shown to inhibit the growth of mammalian tumors when administered as a twice daily dosing schedule. It was found that administration of an FTI in a single dose daily for one to five days produced a marked suppression of tumor growth lasting out to at least 21 days. In some embodiments, FTI is administered at a dosage range of 50-400 mg/kg. In some embodiments, FTI is administered at 200 mg/kg. Dosing regimen for specific FTIs are also well known in the art (e.g., U.S. Pat. No. 6,838,467, which is incorporated herein by reference in its entirety). For example, suitable dosages for the compounds Arglabin (WO98/28303), perrilyl alcohol (WO 99/45712), SCH-66336 (U.S. Pat. No. 5,874,442), L778123 (WO 00/01691), 2(S)-[2(S)-[2(R)-amino-3-mercapto]propylamino-3(S)-methyl]-pentyloxy-3-phenylpropionyl-methionine sulfone (WO94/10138), BMS 214662 (WO 97/30992), AZD3409; Pfizer compounds A and B (WO 00/12499 and WO 00/12498) are given in the aforementioned patent specifications which are incorporated herein by reference or are known to or can be readily determined by a person skilled in the art.

In relation to perrilyl alcohol, the medicament may be administered 1-4 g per day per 150 lb human patient. In one embodiment, 1-2 g per day per 150 lb human patient. SCH-66336 typically may be administered in a unit dose of about 0.1 mg to 100 mg, more preferably from about 1 mg to 300 mg according to the particular application. Compounds L778123 and 1-(3-chlorophenyl)-4-[1-(4-cyanobenzyl)-5-imidazolylmethyl]-2-piperazinone may be administered to a human patient in an amount between about 0.1 mg/kg of body weight to about 20 mg/kg of body weight per day, preferably between 0.5 mg/kg of bodyweight to about 10 mg/kg of body weight per day.

Pfizer compounds A and B may be administered in dosages ranging from about 1.0 mg up to about 500 mg per day, preferably from about 1 to about 100 mg per day in single or divided (i.e. multiple) doses. Therapeutic compounds will ordinarily be administered in daily dosages ranging from about 0.01 to about 10 mg per kg body weight per day, in single or divided doses. BMS 214662 may be administered in a dosage range of about 0.05 to 200 mg/kg/day, preferably less than 100 mg/kg/day in a single dose or in 2 to 4 divided doses.

In some embodiments, the FTI treatment is administered in combination with radiotherapy, or radiation therapy. Radiotherapy includes using γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

In some embodiments, a therapeutically effective amount of the pharmaceutical composition having an FTI is administered that effectively sensitizes a tumor in a host to irradiation. (U.S. Pat. No. 6,545,020, which is hereby incorporated by reference in its entirety). Irradiation can be ionizing radiation and in particular gamma radiation. In some embodiments, the gamma radiation is emitted by linear accelerators or by radionuclides. The irradiation of the tumor by radionuclides can be external or internal.

Irradiation can also be X-ray radiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

In some embodiments, the administration of the pharmaceutical composition commences up to one month, in particular up to 10 days or a week, before the irradiation of the tumor. Additionally, irradiation of the tumor is fractionated the administration of the pharmaceutical composition is maintained in the interval between the first and the last irradiation session.

The amount of FTI, the dose of irradiation and the intermittence of the irradiation doses will depend on a series of parameters such as the type of tumor, its location, the patients' reaction to chemo- or radiotherapy and ultimately is for the physician and radiologists to determine in each individual case.

C. Combination Therapy

In some embodiments, the methods provided herein further include administering a therapeutically effective amount of a second active agent or a support care therapy. The second active agent can be a chemotherapeutic agent. A chemotherapeutic agent or drug can be categorized by its mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabine, navelbine, transplatinum, and pharmaceutically acceptable salts, acids, or derivatives of any of the above.

The second active agents can be large molecules (e.g., proteins) or small molecules (e.g., synthetic inorganic, organometallic, or organic molecules). In some embodiments, the second active agent is a DNA-hypomethylating agent, a therapeutic antibody that specifically binds to a cancer antigen, a hematopoietic growth factor, cytokine, anti-cancer agent, antibiotic, cox-2 inhibitor, immunomodulatory agent, anti-thymocyte globulin, immunosuppressive agent, corticosteroid or a pharmacologically active mutant or derivative thereof.

In some embodiments, the second active agent is a DNA hypomethylating agent, such as a cytidine analog (e.g., azacitidine) or a 5-azadeoxycytidine (e.g. decitabine). In some embodiments, the second active agent is a cytoreductive agent, including but not limited to Induction, Topotecan, Hydrea, PO Etoposide, Lenalidomide, LDAC, and Thioguanine. In some embodiments, the second active agent is Mitoxantrone, Etoposide, Cytarabine, or Valspodar. In some embodiment, the second active agent is Mitoxantrone plus Valspodar, Etoposide plus Valspodar, or Cytarabine plus Valspodar. In some embodiment, the second active agent is idarubicin, fludarabine, topotecan, or ara-C. In some other embodiments, the second active agent is idarubicin plus ara-C, fludarabine plus ara-C, mitoxantrone plus ara-C, or topotecan plus ara-C. In some embodiments, the second active agent is a quinine. Other combinations of the agents specified above can be used, and the dosages can be determined by the physician.

For any specific cancer type described herein, treatments as described herein or otherwise available in the art can be used in combination with the FTI treatment. For example, drugs that can be used in combination with the FTI for PTCL include belinostat (Beleodaq®) and pralatrexate (Folotyn®), marketed by Spectrum Pharmaceuticals, romidepsin (Istodax®), marketed by Celgene, and brentuximab vedotin (Adcetris®) (for ALCL), marketed by Seattle Genetics; drugs that can be used in combination with the FTI for MDS include azacytidine (Vidaza®) and lenalidomide (Revlimid®), marketed by Celgene, and decitabine (Dacogen®) marketed by Otsuka and Johnson & Johnson; drugs that can be used in combination with the FTI for thyroid cancer include AstraZeneca's vandetanib (Caprelsa®), Bayer's sorafenib (Nexavar®), Exelixis' cabozantinib (Cometriq®) and Eisai's lenvatinib (Lenvima®).

Non-cytotoxic therapies such as tpralatrexate (Folotyn®), romidepsin (Istodax®) and belinostat (Beleodaq®) can also be used in combination with the FTI treatment.

In some embodiments, it is contemplated that the second active agent or second therapy used in combination with a FTI can be administered before, at the same time, or after the FTI treatment. In some embodiments, the second active agent or second therapy used in combination with a FTI can be administered before the FTI treatment. In some embodiments, the second active agent or second therapy used in combination with a FTI can be administered at the same time as FTI treatment. In some embodiments, the second active agent or second therapy used in combination with a FTI can be administered after the FTI treatment.

The FTI treatment can also be administered in combination with a bone marrow transplant. In some embodiments, the FTI is administered before the bone marrow transplant. In other embodiments, the FTI is administered after the bone marrow transplant.

A person of ordinary skill in the art would understand that the methods described herein include using any permutation or combination of the specific FTI, formulation, dosing regimen, additional therapy to treat a subject described herein.

In some embodiments, the subject having PTCL who is selected for tipifarnib treatment receives a dose of 900 mg b.i.d. orally in alternate weeks (one week on, one week off) in repeated 4 week cycles.

In some embodiments, the subject having PTCL who is selected for tipifarnib treatment receives a dose of 600 mg b.i.d. orally in alternate weeks (one week on, one week off) in repeated 4 week cycles.

It is understood that modifications which do not substantially affect the activity of the various embodiments of this invention are also provided within the definition of the invention provided herein. Accordingly, the following examples are intended to illustrate but not limit the present invention. All of the references cited to herein are incorporated by reference in their entireties.

EXAMPLE I

Tipifarnib Clinical Study in PTCL Patients

A Phase II clinical study of tipifarnib can be conducted with the primary objective being to assess the antitumor activity of tipifarnib, in terms of Objective Response Rate (ORR) in subjects with relapsed or refractory advanced peripheral T-cell lymphoma (PTCL). Determination of objective tumor response can be performed by the International Workshop Criteria (IWC) and/or measurable cutaneous disease according to the modified Severity Weighted Assessment Tool (mSWAT). Secondary objectives can include accessing the effect of tipifarnib on rate of progression-free survival (PFS) at 1 year, duration of response (DOR), overall survival (OS); and safety and tolerability of tipifarnib.

This Phase II study investigates the antitumor activity in terms of ORR of tipifarnib in subjects with PTCL. Up to 18 eligible subjects with advanced PTCL are enrolled. The total number of patients can be extended to 30.

Subjects receive tipifarnib administered at a starting dose of 900 mg, orally with food, twice a day (bid) for 7 days in alternating weeks (Days 1-7 and 15-21) in 28 day cycles. At the discretion of the investigator, the dose of tipifarnib can be increased to 1200 mg bid if the subject has not experienced dose limiting toxicities at the 900 mg dose level. Subjects who develop serious adverse events (SAE) or ≥grade 2 treatment-emergent adverse events (TEAE) that are deemed related to tipifarnib and lasting ≥14 days will not undergo dose escalation. Stepwise 300 mg dose reductions to control treatment-related, treatment-emergent toxicities are also allowed.

In the absence of unmanageable toxicities, subjects can continue to receive tipifarnib treatment until disease progression. If a complete response is observed, therapy with tipifarnib can be maintained for at least 6 months beyond the start of response.

Tumor assessments are performed at screening and at least once every approximately 8 weeks for 6 months (cycles 2, 4, 6) and once every approximately 12 weeks (cycles 9, 12, 15, etc.) thereafter, until disease progression, starting at the end of Cycle 2. Additional tumor assessments can be conducted if deemed necessary by the Investigator. Subjects who discontinue tipifarnib treatment for reasons other than disease progression must continue tumor assessments until disease progression, withdrawal of subject's consent to study

EXAMPLE II

Evidence of Activity in Tipifarnib Clinical Study in PTCL Patients

Evidence of clinical activity was studied in a cohort of patients enrolled in the study described in Example I. Durable responses (11 months median) were seen in 4 out of 8 PTCL patients.

The study was an eighteen patient Phase II study with a Simon two-stage design (11+7). Two responses were required after the first eleven evaluable patients in order to proceed to second stage. Enrollment is to be extended to thirty patients if five responses are seen in the first stage.

The dose of 900 mg b.i.d. for seven days in alternate week dosing was amended during the first stage to 600 mg b.i.d. for seven days in alternate week dosing.

FIG. 1 shows the number of cycles received by each of the eighteen patients dosed at a first time point during the study. Each of the eighteen patients and the type of PTCL is listed in Table 1, along with the outcomes. Three partial responses (PRs) were observed. Of the two subjects with AITL, both showed PRs. Three patients are ongoing, indicated by arrows in FIG. 1, and two patients have had greater than six months of stable disease.

partial responses (PRs) were observed. Of the two subjects with AITL, both showed PRs. Two patients are ongoing, indicated by arrows in FIG. 1, and four patients have had greater than six months of stable disease.

Formalin-fixed, paraffin-embedded (FFPE) samples were obtained from all subjects for the analysis of gene expression using RNA Seq and of single nucleotide variation (SNV, including SNPs and mutations) using next generation sequencing (NGS). Thirteen samples passed quality control (QC) for expression analysis. Sixteen samples passed quality control for SNV analysis.

The expression of CXCL12 and CXCR4, as well as the ratio of the expression of CXCL12 to CXCR4, was measured in thirteen of the subjects, as shown in Table 1. Subjects with a CXCL12/CXCR4 ratio greater than 0.200 had PR or stable disease (SD). Subjects with a CXCL12/

TABLE 1

Subject outcomes and expression characteristics for tipifarnib clinical study in PTCL patients.

| Subject | Tumor Histology | SNVs | Response | CXCL12 expression | CXCR4 expression | CXCL12/CXCR4 Ratio | KIR3DL2 expression | VCAM1 expression | CXCL13 expression |
|---|---|---|---|---|---|---|---|---|---|
| 1 | PTCL-NOS | rs2839695 | PD | | | | | | |
| 2 | PTCL-NOS | CENPF R2729Q; SIK3 variant | SD | 3728 | 9329 | 0.4 | 76 | 4785 | 424 |
| 3 | AITL | SIK3 variant | PR | 14076 | 1898 | 7.416 | 125 | 29134 | 1176 |
| 4 | PTCL-NOS | 3'UTR CXCL12 SNV position 44873186; CENPF R2729Q | PD | 1081 | 6408 | 0.169 | 58 | 5344 | 2088 |
| 5 | ALCL-ALK | rs2839695; SIK3 variant | PD | 1211 | 8637 | 0.14 | 2 | 546 | 10 |
| 6 | PTCL-NOS | rs2839695 | PD | 834 | 10668 | 0.078 | 33625 | 5746 | 715 |
| 7 | PTCL-NOS | rs2839695 | PD | 325 | 11282 | 0.029 | 18533 | 1255 | 47 |
| 8 | PTCL-NOS | rs2839695 | PD | | | | | | |
| 9 | PTCL-NOS | N/A | PD | | | | | | |
| 10 | PTCL-NOS | rs2839695; CENPF R2729Q; SIK3 variant | PD | 1570 | 8890 | 0.177 | 178 | 2874 | 16876 |
| 11 | AITL | CENPF R2729Q; SIK3 variant | PR | 3265 | 9274 | 0.352 | 6 | 7359 | 25355 |
| 12 | PTCL-NOS | | PD | 759 | 4866 | 0.156 | 2457 | 2328 | 303 |
| 13 | PTCL-NOS | CENPF R2729Q; SIK3 variant | SD | | | | | | |
| 14 | PTCL-NOS | | PD | 613 | 6256 | 0.098 | 5 | 1776 | 351 |
| 15 | PTCL-NOS | N/A | PR | | | | | | |
| 16 | PTCL-NOS | rs2839695; SIK3 variant | PD | 469 | 14617 | 0.032 | 6810 | 3643 | 4602 |
| 17 | PTCL-NOS | CENPF R2729Q; SIK3 variant | SD | 1160 | 3811 | 0.304 | 29 | 1118 | 1039 |
| 18 | PTCL-NOS | CENPF R2729Q; SIK3 variant | SD | 2659 | 3118 | 0.853 | 11 | 4111 | 1729 |

Figure 2:
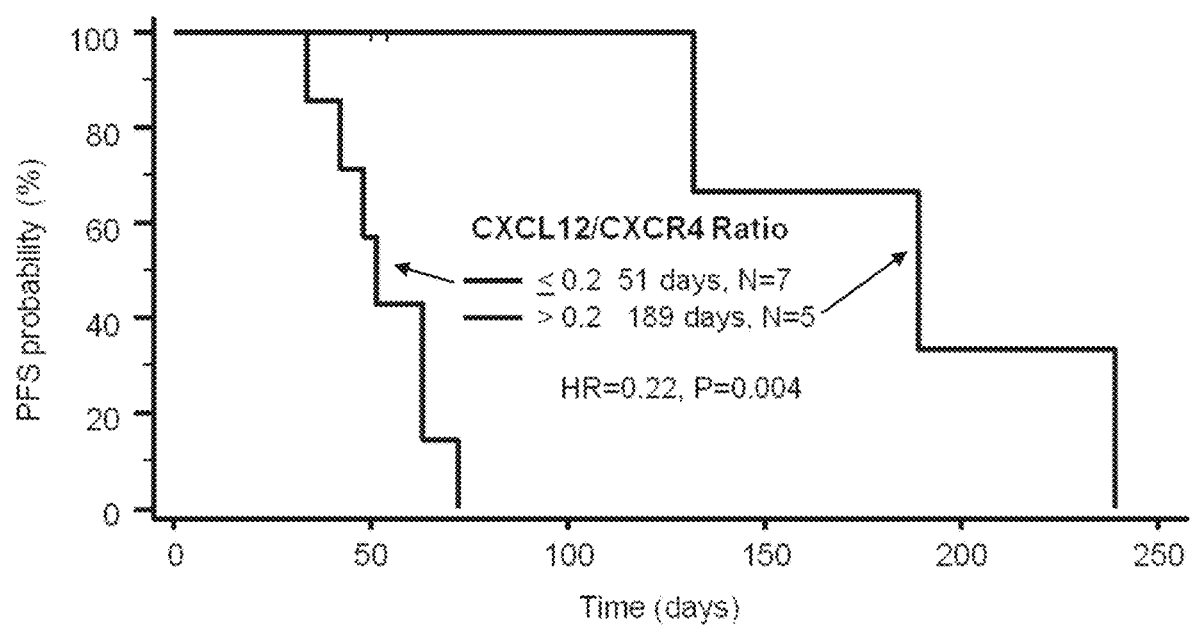
FIG. 2. Progression free survival (PFS) probability over time (days) for CXCL12/CXCR4 ratio of less than or equal to 0.200 (median PFS (mPFS) of 51 days) and greater than 0.200 (mPFS of 189 days).
Figure 5:
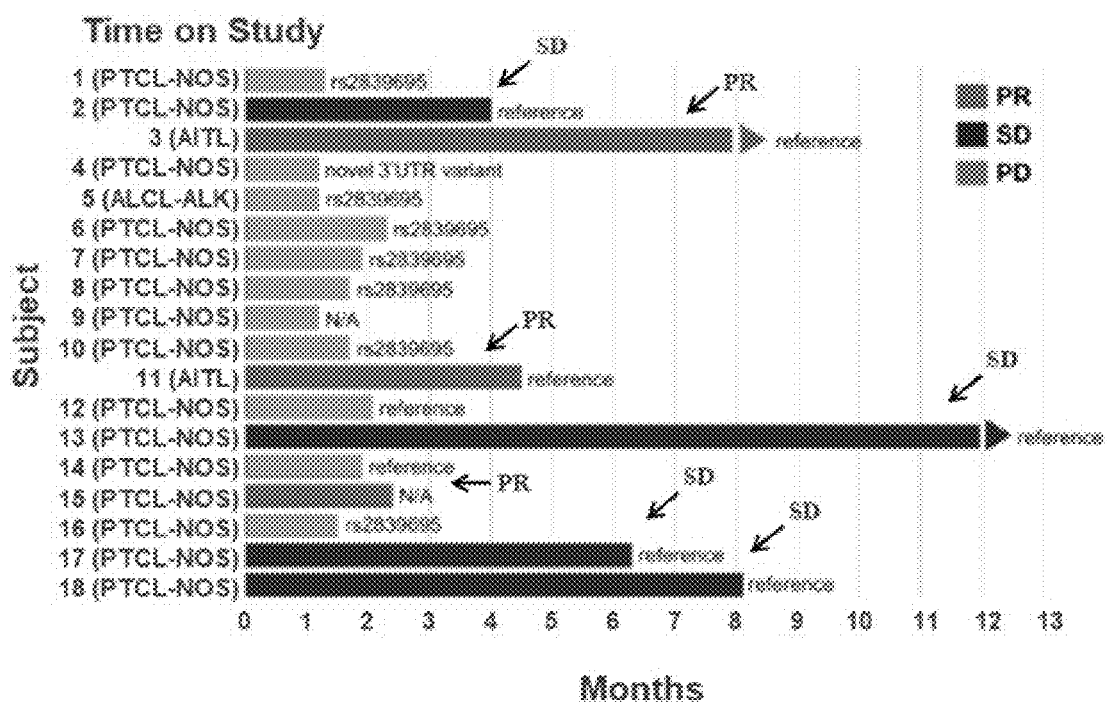
FIG. 5. Number of cycles of treatment received by PTCL-NOS, PTCL-AITL, or ALCL-ALK subjects in the PTCL tipifarnib clinical study. Arrows indicate ongoing treatment. PR: partial response; SD: stable disease; PD: progressive disease.

FIG. 5 shows the number of cycles received by each of the eighteen patients dosed at a later second time point during the study. The type of PTCL and the SNV status is indicated in FIG. 5 for each patient, along with the outcomes. Three CXCR4 ratio less than or equal 0.200 did not show PR or SD, as shown in Table 1. The median progression free survival (mPFS) for patients with a CXCL12/CXCR4 ratio >0.200 was 189 days (N=5), whereas the mPFS for patients with a CXCL12/CXCR4 ratio ≤0.200 was 51 days (N=7), as shown in FIG. 2 (HR=0.22; P=0.004). The expression of VCAM1 and CXCL13 was also measured in those thirteen subjects.

Figure 3:
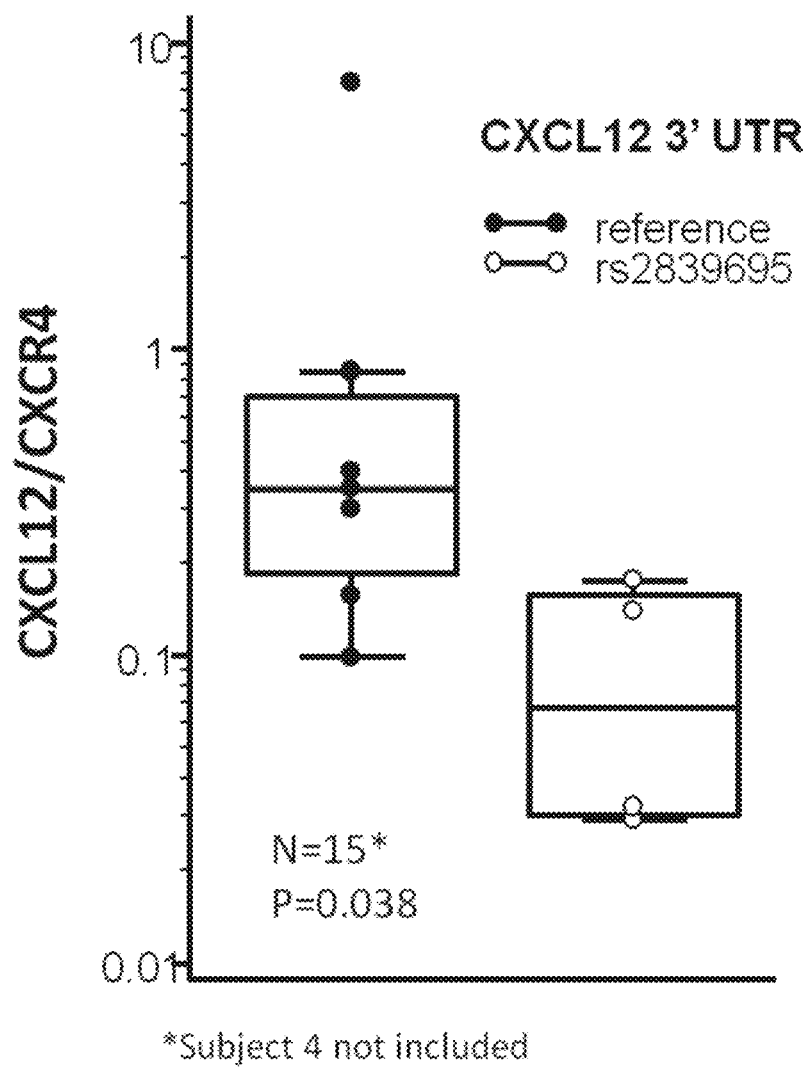
FIG. 3. CXCL12/CXCR4 expression ratio for subjects with CXCL12 3' UTR SNV rs2839695 (open circles) versus subjects with reference CXCL12 3' UTR (closed circles).
Figure 4:
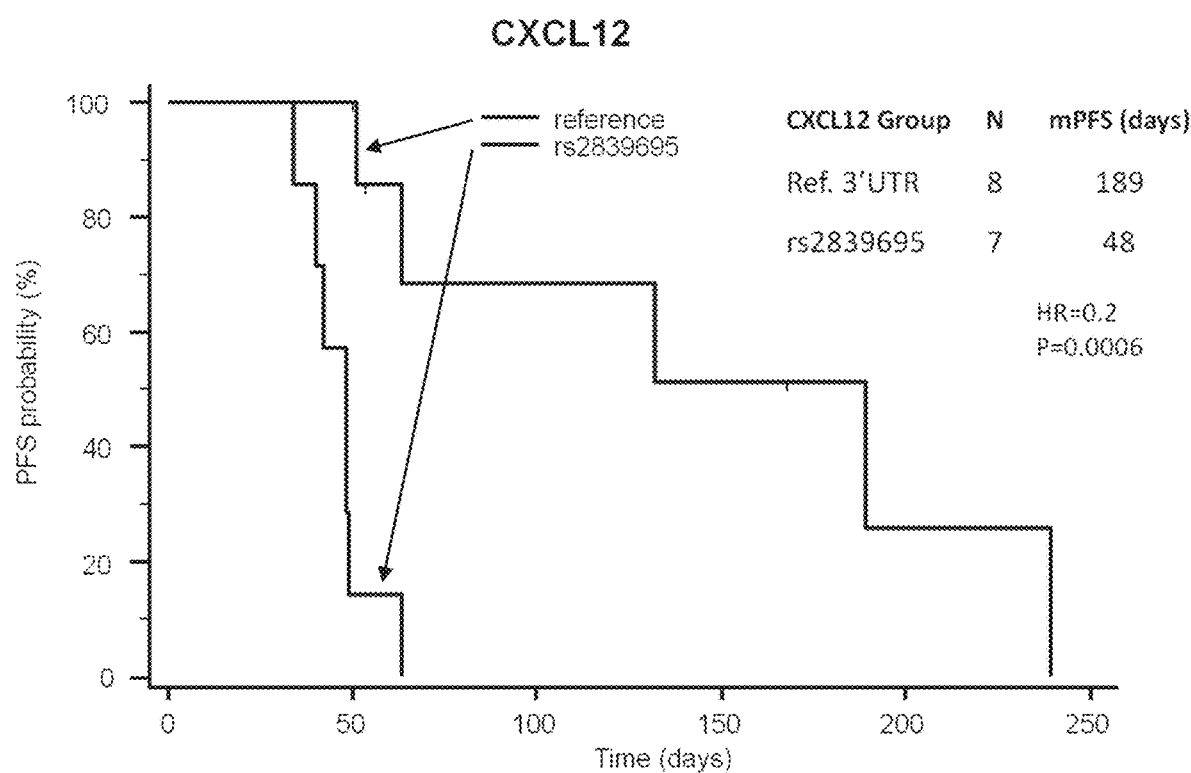
FIG. 4. Progression free survival (PFS) probability over time (days) for subjects with CXCL12 3' UTR SNV rs2839695 (mPFS of 48 days) versus subjects with reference CXCL12 3' UTR (mPFS of 189 days)
Figure 6:
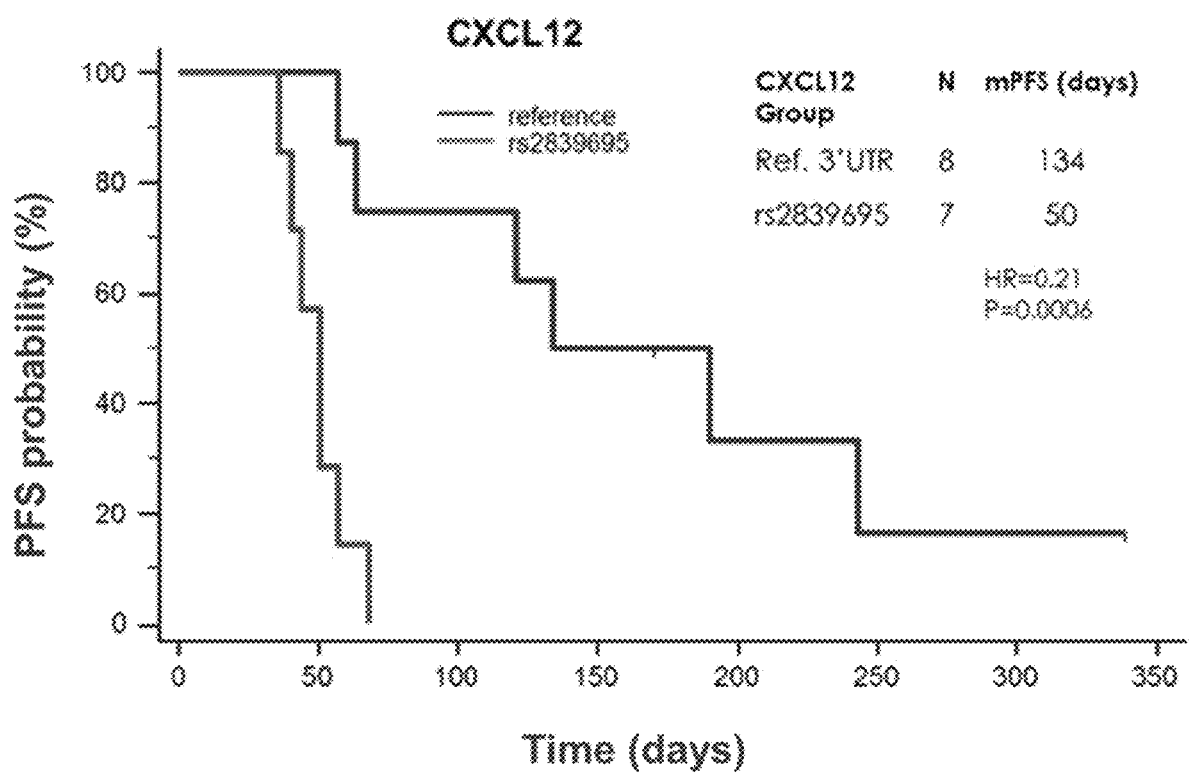
FIG. 6. Progression free survival (PFS) probability over time (days) for subjects with CXCL12 3' UTR SNV rs2839695 (mPFS of 50 days) versus subjects with reference CXCL12 3' UTR (mPFS of 134 days)

Eight subjects (50%) of the sixteen for which NGS passed QC carried SNVs in the 3' UTR of the CXCL12 gene. Seven were carriers of rs2839695 (A/G at position 44873849 in the CXCL12 3' UTR). One subject carried both rs2839695 and a novel 3' UTR SNV at position 44866733. One additional subject carried a novel 3' UTR SNV at position 44873186. Tumors carrying rs2839695 had lower CXCL12/CXCR4 ratios, as seen in FIG. 3 and in Table 1. Subject 4, which had the novel 3' UTR SNV at position 44873186, presented a very low CXCL12/CXCR4 ratio. The frequency of 3'UTR SNVs (0.5) was unusual. The expected frequencies of rs2839695 across the general populations are as follows: 1000G_AFR=0.2; 1000G ANIR=0.097; 1000G EAS=0.001; 1000G EUR=0.2; 1000G SAS=0.045. CXCL12 rs2839695 was associated with poor prognosis in tipifarnib treated PTCL, as shown in FIG. 4. The mPFS for those patients with no SNV in the 3' UTR of CXCL12 was 189 days (N=8), whereas those patients with CXCL12 rs2839695 had an mPFS of 48 days (N=7). At a later timepoint during the study, the mPFS for those patients with no SNV in the 3' UTR of CXCL12 was 134 days (N=8), whereas those patients with CXCL12 rs2839695 had an mPFS of 50 days (N=7), as shown in FIG. 6.

Figure 7:
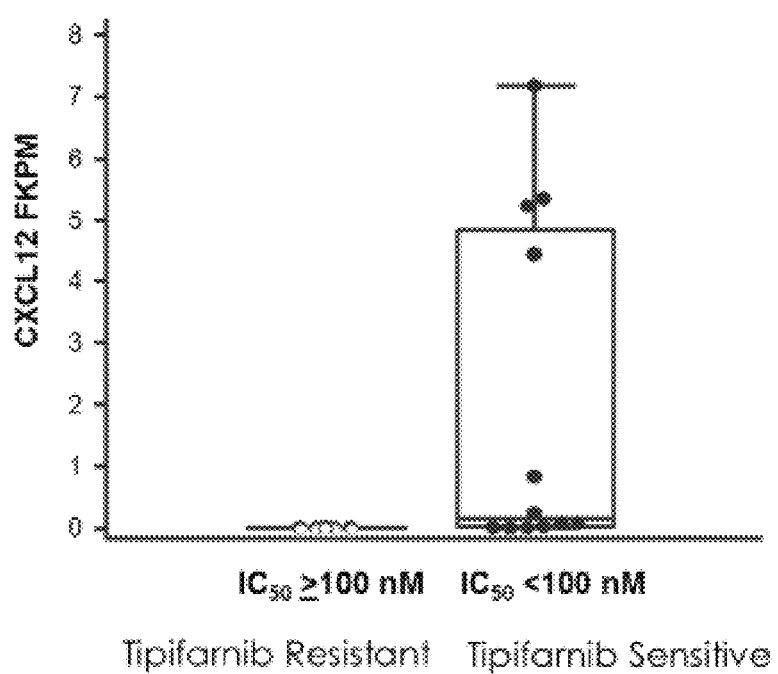
FIG. 7. CXCL12 expression in tipifarnib resistant and tipifarnib sensitive T-cell leukemia and lymphoma (T-LL) cell lines.
Figure 8:
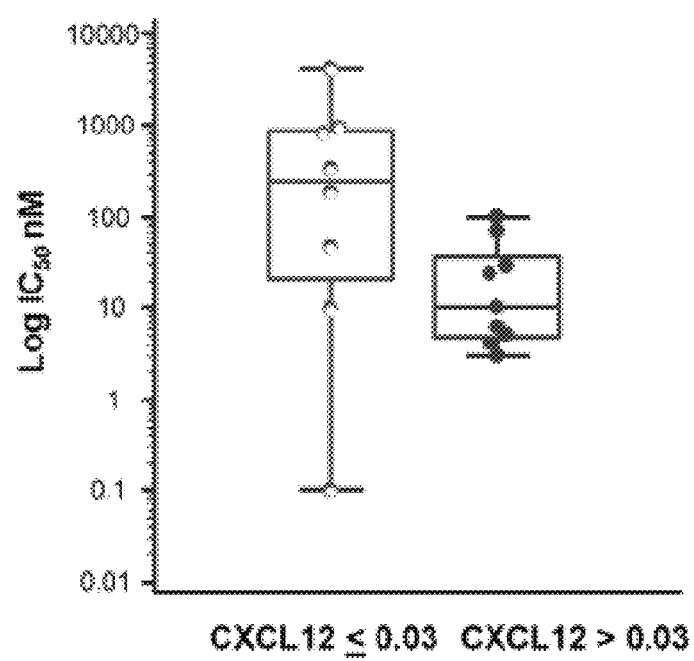
FIG. 8. Tipifarnib potency (IC50) in T-LL cell lines depending on CXCL12 expression levels.

FIG. 7 and FIG. 8 show results of in vitro experiments with T-cell leukemia and lymphoma cell lines, which further demonstrate that CXCL12 expression and CXCL12 3'UTR gene variation can be useful as biomarkers of tipifarnib's activity in PTCL. FIG. 7. shows that CXCL20 is expressed in certain tipifarnib sensitive T-LL cell lines and not detectable in other T-LL cell lines that are tipifarnib resistant. FIG. 8 shows that the potency of tipifarnib is higher (IC50 is lower) with T-LL cells showing higher CXCL12 expression than with T-LL cells showing lower CXCL12 expression.

Table 1 also shows the KIR3DL2 expression levels for 13 subjects. Subjects with high KIR3DL2 expression (e.g., over 1000) did not show PR or SD. Thus, it appears that tipifarnib shows no activity in KIR3DL2-expressing PTCL.

The CENPF gene variant R2729Q was observed in 7 of 16 subjects (44%) (Table 1). Five of six subjects with a best response of PR/SD and 2 of 10 subjects with a best response of PD (no qualified sample was obtained in 2 subjects) carried R2729Q. The overall frequency of R2729Q in the American population is 59%.

SNPs located in the N-terminal coding sequence of SIK3 (S986Y, P1076R, P1136R (5 subjects), S1163G) were observed in 8 subjects (Table 1). An additional subject had a tumor with a N559H mutation (50% total variation). 6 of 6 subjects with a best response of PR/SD and 3 of 11 subjects with a best response of PD carried SIK3 SNVs. The overall frequency of SIK3 gene SNVs in the American population is 19%.

EXAMPLE III

Individualized FTI Treatment Decisions

The following procedures can be taken to determine whether a patient is suitable for an FTI treatment, such as a tipifarnib treatment.

Immunostaining for CXCL12, CXCR4, and/or KIR3DL2 can be performed on formalin-fixed, paraffin-embedded tissue sections from patients following microwave antigen retrieval in a 1-mmol/L concentration of EDTA, pH 8.0, with a human CXCL12, CXCR4, and/or KIR3DL2 monoclonal antibody known in the art, using a standard indirect avidin-biotin horseradish peroxidise method and diaminobenzidine color development as is well-known in the art. Staining can be compared with that of mouse IgG isotype control antibody diluted to identical protein concentration for all cases studied, to confirm staining specificity.

The patient may also be tested for circulating CXCL12, for example, in a serum sample. Biopsy samples may also be tested for EBV biomarkers such as CXCL13 and PD-1.

T-cells can be isolated from the Peripheral blood mononuclear cells (PBMCs) obtained from patient serum. Total RNA can be extracted from cell samples using the Trizol Kit (Qiagen, Santa Clarita, Calif.). RNA quality can be determined by assessing the presence of ribosomal bands on an Agilent Bioanalyzer (Agilent, Palo Alto, Calif.). Good-quality samples can be used for reverse transcription (RT) reactions using the High Capacity cDNA Reverse Transcription Kit (Applied Biosystems, Foster City, Calif.) according to the manufacturer's instructions. Quantitative RT-PCR (qRT-PCR) can be performed for CXCL12, CXCR4, SIK3, and/or CENPF using the ABI Prism 7900HT Sequence Detection System (Applied Biosystems) with all samples run in triplicate. A negative control without cDNA template can be run with every assay. Transcript copy number per individual can be calculated by normalization to EEF1A1 expression.

If the cancer patient, for example, the PTCL patient, is determined to have high CXCL12 expression, and/or if the cancer patient, for example, the PTCL patient, is determined to have high levels of CXCL12 and low levels of CXCR4 and if the patient is not otherwise prevented from receiving a tipifarnib treatment, a tipifarnib treatment is prescribed. On the other hand, if the cancer patient, for example, the PTCL patient, is determined to not have either high CXCL12 expression, or if the cancer patient, for example, the PTCL patient, is determined to have low levels of CXCL12 or high levels of CXCR4, a tipifarnib treatment is not recommended.

If the cancer patient, for example, the PTCL patient, is determined to have a SIK3 gene variant expression or a CENPF R2729Q variant expression and if the patient is not otherwise prevented from receiving a tipifarnib treatment, a tipifarnib treatment is prescribed.

If the cancer patient, for example, the PTCL patient, is determined to have KIR3DL2 expression a tipifarnib treatment is not recommended.

If the cancer patient, for example, the PTCL patient, is determined to have a 3' UTR CXCL12 single nucleotide variant, a tipifarnib treatment is not recommended. DNA for the determination of a 3' UTR CXCL12 variant can be obtained from tumor biopsies, lymph node biopsies, bone marrow aspirates, blood samples, PBMC obtained from blood samples or buccal swaps.

If a tipifarnib treatment is prescribed to the cancer patient, for example, the PTCL patient, the cancer patient, for example, the PTCL patient, can simultaneously receive another treatment, such as ionizing radiation, or a second active agent or a support care therapy, as deemed fit by the oncologist. The second active agent can be a DNA-hypomethylating agent, such as azacitidine or decitabine

EXAMPLE IV

Evidence of Activity in Tipifarnib Clinical Study in AML Patients

Previous clinical studies with tipifarnib were performed in newly diagnosed AML in elderly patients with poor risk AML (CTEP-20, Phase 2) or relapsed and refractory AML (INT-17, Phase 2). In these studies, patient selection was not based on genetic markers. Anecdotal evidence of tipifarnib single agent activity was reported. However, overall clinical activity across the patient population did not support tipifarnib registration.

Figure 9:
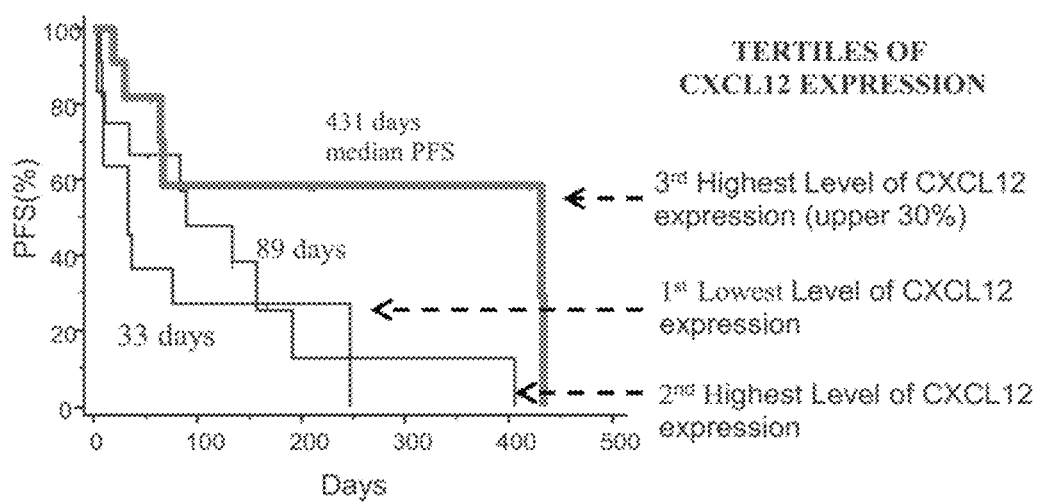
FIG. 9. Progression free survival (PFS) probability over time (days) for newly-diagnosed elderly, frail AML patients in different textiles of CXCL12 expression (CTEP-20 trial, Phase 2).
Figure 10:
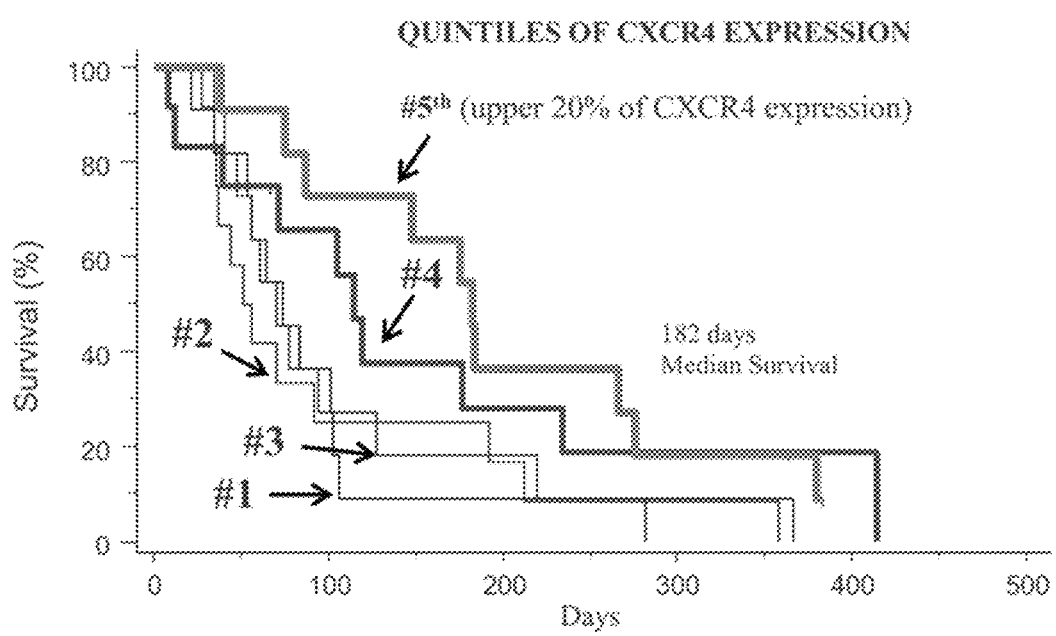
FIG. 10. Progression free survival (PFS) probability over time (days) for relapsed/refractory AMP patients in different quintiles of CDCR4 expression (INT17 trial, Phase 2).

Analysis of mRNA expression profiling data from patients in the CTEP-20 and INT-17 trials showed that tipifarnib efficacy was higher in patients with relatively elevated CXCL12/CXCR4 expression ratios. FIG. 9 shows that treatment naïve elderly, frail AML patients in the highest CXCL12 expression tertile (highest level of CXCL12 expression) experienced 431 days of median progression free survival (mPFS), patients in the second tertile experiences 89 days mPFS, and patients in the third tertile (lowest level of CXCL12 expression) experienced 33 days mPFS under the same tipifarnib treatment regimen. FIG. 10 shows that the relapsed or refractory AML patients in the highest quintile of CXCR4 expression experienced 182 days of median survival, which is about double the median survival of patients in the lowest CXCR4 expression quintile.

These results demonstrate that AML patient benefiting from tipifarnib can be identified and selected for tipifarnib treatment based on the patients' CXCL12 and CXCR4 expression levels.

We claim:

1. A method of treating an angioimmunoblastic T-cell lymphoma (AITL) in a subject, comprising administering a therapeutically effective amount of a farnesyltransferase inhibitor (FTI) to the subject.

2. The method of claim 1, wherein the AITL is relapsed or refractory AITL.

3. The method of claim 1, wherein FTI is selectively administered to the subject on the basis that the subject has a tumor of AITL histology.

4. The method of claim 3, wherein the AITL histology is characterized by a tumor cell component.

5. The method of claim 4, wherein the tumor cell component comprises polymorphous medium-sized neoplastic cells derived from follicular helper T cells.

6. The method of claim 3, wherein the AITL histology is characterized by a non-tumor cell component.

7. The method of claim 6, wherein the non-tumor cell component comprises prominent arborizing blood vessels.

8. The method of claim 7, wherein the non-tumor cell component comprises proliferation of follicular dendritic cells.

9. The method of claim 8, wherein the non-tumor cell component comprises scattered EBV positive B-cell blasts.

10. The method of claim 1, wherein the subject having AITL has been diagnosed with AITL.

11. The method of claim 10, wherein diagnosis with AITL comprises visualization of a non-tumor component.

12. The method of claim 10, wherein diagnosis with AITL comprises visualization of proliferation of endothelial venules.

13. The method of claim 10, wherein diagnosis with AITL comprises detecting the presence of one or more of the following tumor markers: CXCL13, CD10, PD1, and BCL6.

14. The method of claim 1, wherein FTI is administered orally, parenterally, rectally, or topically.

15. The method of claim 1, wherein FTI is administered at a dose of 0.05-500 mg/kg body weight.

16. The method of claim 1, wherein FTI is administered twice a day.

17. The method of claim 1, wherein FTI is administered at a dose of 200-1200 mg twice a day.

18. The method of claim 17, wherein the FTI is administered at a dose of 100 mg, 200 mg, 300 mg, 400 mg, 600 mg, 900 mg or 1200 mg twice a day.

19. The method of claim 1, wherein the FTI is administered on days 1-7 and 15-21 of a 28-day treatment cycle.

20. The method of claim 1, wherein the FTI is administered on days 1-21 of a 28-day treatment cycle.

21. The method of claim 1, wherein the FTI is administered on days 1-7 of a 28-day treatment cycle.

22. The method of claim 20, wherein FTI is administered at a dose of 900 mg twice a day.

23. The method of claim 20, wherein FTI is administered at a dose of 600 mg twice a day.

24. The method of claim 20, wherein FTI is administered at a dose of 400 mg twice a day.

25. The method of claim 20, wherein FTI is administered at a dose of 300 mg twice a day.

26. The method of claim 20, wherein FTI is administered at a dose of 200 mg twice a day.

27. The method of claim 1, wherein FTI is administered before, during, or after radiation.

28. The method of claim 1, further comprising administering a therapeutically effective amount of a second active agent or a support care therapy.

29. The method of claim 28, wherein the second active agent is a histone deacetylase, an antifolate, or chemotherapy.

30. The method of claim 1, that consists of administering a therapeutically effective amount of FTI to the subject.

* * * * *